US012718918B2

(12) United States Patent
Narayanaswami

(10) Patent No.: US 12,718,918 B2
(45) Date of Patent: Aug. 25, 2026

(54) MEDICAMENT ADAPTATION AND SAFETY MONITORING

(71) Applicant: INSULET CORPORATION, Acton, MA (US)

(72) Inventor: Rangarajan Narayanaswami, Weston, MA (US)

(73) Assignee: INSULET CORPORATION, Acton, MA (US)

( * ) Notice: Subject to any disclaimer, the term of this patent is extended or adjusted under 35 U.S.C. 154(b) by 667 days.

(21) Appl. No.: 18/137,186

(22) Filed: Apr. 20, 2023

(65) Prior Publication Data

US 2023/0343430 A1 Oct. 26, 2023

Related U.S. Application Data

(60) Provisional application No. 63/333,149, filed on Apr. 21, 2022.

(51) Int. Cl.
*G16H 20/10* (2018.01)
*A61B 5/145* (2006.01)
(Continued)

(52) U.S. Cl.
CPC ......... *G16H 20/10* (2018.01); *A61B 5/14532* (2013.01); *A61B 5/14546* (2013.01);
(Continued)

(58) Field of Classification Search
CPC ........ G16H 20/10; G16H 20/30; G16H 20/60; G16H 40/67; A61B 5/14532;
(Continued)

(56) References Cited

U.S. PATENT DOCUMENTS 303,013 A 8/1884 Horton
441,663 A 12/1890 Hofbauer
(Continued)

FOREIGN PATENT DOCUMENTS

AU 2015200834 A1 3/2015
AU 2015301146 A1 3/2017
(Continued)

OTHER PUBLICATIONS

US 5,954,699 A, 09/1999, Jost et al. (withdrawn)
(Continued)

*Primary Examiner* — David P. Olynick
(74) *Attorney, Agent, or Firm* — Goodwin Procter LLP

(57) ABSTRACT

Disclosed are exemplary drug delivery systems that include controllers, drug delivery devices, and the like. The disclosed drug delivery system and controllers may include a processor, a user interface, a memory, and communication circuitry. An automated drug delivery algorithm is operable to receive a number of different inputs related to a user's glucose and/or ketone levels. The automated drug delivery algorithm(s) of the described drug delivery systems and controllers are operable to adjust to when a user partakes in fasting for a period of time that lasts a day or multiple days. The period of time may be a fasting event, such as a religious holiday or diet regimen. For example, the disclosed automated drug delivery algorithm(s) are operable to receive an indication of initiation of a fasting mode; and modify a drug delivery schedule based on the period of fasting or while in fasting mode.

18 Claims, 10 Drawing Sheets

(51) Int. Cl.
*A61M 5/142* (2006.01)
*A61M 5/172* (2006.01)

(52) U.S. Cl.
CPC ....... *A61M 5/1723* (2013.01); *A61M 5/14248* (2013.01); *A61M 2202/0486* (2013.01); *A61M 2205/3303* (2013.01); *A61M 2205/502* (2013.01); *A61M 2205/52* (2013.01); *A61M 2230/201* (2013.01)

(58) Field of Classification Search
CPC ............ A61B 5/14546; A61M 5/1723; A61M 5/14248; A61M 2202/0486; A61M 2205/3303; A61M 2205/502; A61M 2205/52; A61M 2230/201
See application file for complete search history.

(56) References Cited

U.S. PATENT DOCUMENTS 445,545 A 2/1891 Crane
588,583 A 8/1897 Lade
955,911 A 4/1910 Saegmuller
1,441,508 A 1/1923 Marius
2,283,925 A 5/1942 Harvey
2,797,149 A 6/1957 Skeggs
2,886,529 A 5/1959 Guillaud
3,574,114 A 4/1971 Monforte
3,614,554 A 10/1971 Shield
3,631,847 A 1/1972 Hobbs
3,634,039 A 1/1972 Brondy
3,812,843 A 5/1974 Wootten et al.
3,841,328 A 10/1974 Jensen
3,885,662 A 5/1975 Schaefer
3,963,380 A 6/1976 Thomas, Jr. et al.
3,983,077 A 9/1976 Fuller et al.
4,055,175 A 10/1977 Clemens et al.
4,108,177 A 8/1978 Pistor
4,146,029 A 3/1979 Ellinwood, Jr.
4,151,845 A 5/1979 Clemens
4,206,401 A 6/1980 Meyer
4,245,634 A 1/1981 Albisser et al.
4,268,150 A 5/1981 Chen
4,277,226 A 7/1981 Archibald
4,307,713 A 12/1981 Galkin et al.
4,313,439 A 2/1982 Babb et al.
4,368,980 A 1/1983 Aldred et al.
4,373,527 A 2/1983 Fischell
4,398,542 A 8/1983 Cunningham et al.
4,400,683 A 8/1983 Eda et al.
4,403,984 A 9/1983 Ash et al.
4,424,720 A 1/1984 Bucchianeri
4,435,173 A 3/1984 Siposs et al.
4,464,170 A 8/1984 Clemens et al.
4,469,481 A 9/1984 Kobayashi
4,475,901 A 10/1984 Kraegen et al.
4,498,843 A 2/1985 Schneider et al.
4,507,115 A 3/1985 Kambara et al.
4,523,170 A 6/1985 Huth, III
4,526,568 A 7/1985 Clemens et al.
4,526,569 A 7/1985 Bernardi
4,529,401 A 7/1985 Leslie et al.
4,551,134 A 11/1985 Slavik et al.
4,559,033 A 12/1985 Stephen et al.
4,559,037 A 12/1985 Franetzki et al.
4,560,979 A 12/1985 Rosskopf
4,562,751 A 1/1986 Nason et al.
4,573,968 A 3/1986 Parker
4,585,439 A 4/1986 Michel
4,587,850 A 5/1986 Moser
4,601,707 A 7/1986 Albisser et al.
4,624,661 A 11/1986 Arimond
4,633,878 A 1/1987 Bombardieri
4,634,427 A 1/1987 Hannula et al.
4,646,038 A 2/1987 Wanat
4,657,529 A 4/1987 Prince et al.
4,678,408 A 7/1987 Nason et al.
4,684,368 A 8/1987 Kenyon
4,685,903 A 8/1987 Cable et al.
4,731,726 A 3/1988 Allen, III
4,743,243 A 5/1988 Vaillancourt
4,755,169 A 7/1988 Sarnoff et al.
4,755,173 A 7/1988 Konopka et al.
4,759,120 A 7/1988 Bernstein
4,781,688 A 11/1988 Thoma et al.
4,781,693 A 11/1988 Martinez et al.
4,801,957 A 1/1989 Vandemoere
4,808,161 A 2/1989 Kamen
4,836,752 A 6/1989 Burkett
4,850,954 A 7/1989 Charvin
4,854,170 A 8/1989 Brimhall et al.
4,859,492 A 8/1989 Rogers, Jr. et al.
4,880,770 A 11/1989 Mir et al.
4,882,600 A 11/1989 Van de Moere
4,886,499 A 12/1989 Cirelli et al.
4,898,578 A 2/1990 Rubalcaba, Jr.
4,898,579 A 2/1990 Groshong et al.
4,900,292 A 2/1990 Berry et al.
4,919,596 A 4/1990 Slate et al.
4,925,444 A 5/1990 Orkin et al.
4,940,527 A 7/1990 Kazlauskas et al.
4,944,659 A 7/1990 Labbe et al.
4,961,055 A 10/1990 Habib et al.
4,967,201 A 10/1990 Rich, III
4,969,874 A 11/1990 Michel et al.
4,973,998 A 11/1990 Gates
4,975,581 A 12/1990 Robinson et al.
4,976,720 A 12/1990 Machold et al.
4,981,140 A 1/1991 Wyatt
4,994,047 A 2/1991 Walker et al.
5,007,286 A 4/1991 Malcolm et al.
5,007,458 A 4/1991 Marcus et al.
5,045,871 A 9/1991 Reinholdson
5,062,841 A 11/1991 Siegel
5,084,749 A 1/1992 Losee et al.
5,097,834 A 3/1992 Skrabal
5,102,406 A 4/1992 Arnold
5,109,850 A 5/1992 Blanco et al.
5,125,415 A 6/1992 Bell
5,130,675 A 7/1992 Sugawara
5,134,079 A 7/1992 Cusack et al.
5,139,999 A 8/1992 Gordon et al.
5,153,827 A 10/1992 Coutre et al.
5,154,973 A 10/1992 Imagawa et al.
5,165,406 A 11/1992 Wong
5,176,662 A 1/1993 Bartholomew et al.
5,178,609 A 1/1993 Ishikawa
5,189,609 A 2/1993 Tivig et al.
5,198,824 A 3/1993 Poradish
5,205,819 A 4/1993 Ross et al.
5,207,642 A 5/1993 Orkin et al.
5,213,483 A 5/1993 Flaherty et al.
5,217,754 A 6/1993 Santiago-Aviles et al.
5,219,377 A 6/1993 Poradish
5,232,439 A 8/1993 Campbell et al.
5,237,993 A 8/1993 Skrabal
5,239,326 A 8/1993 Takai
5,244,463 A 9/1993 Cordner, Jr. et al.
5,254,096 A 10/1993 Rondelet et al.
5,257,980 A 11/1993 Van Antwerp et al.
5,261,882 A 11/1993 Sealfon
5,263,198 A 11/1993 Geddes et al.
5,272,485 A 12/1993 Mason et al.
5,273,517 A 12/1993 Barone et al.
5,281,202 A 1/1994 Weber et al.
5,281,808 A 1/1994 Kunkel
5,299,571 A 4/1994 Mastrototaro
5,308,982 A 5/1994 Ivaldi et al.
5,342,298 A 8/1994 Michaels et al.
5,346,476 A 9/1994 Elson
5,364,342 A 11/1994 Beuchat et al.
5,377,674 A 1/1995 Kuestner
5,380,665 A 1/1995 Cusack et al.
5,385,539 A 1/1995 Maynard

(56) References Cited

U.S. PATENT DOCUMENTS 5,389,078 A 2/1995 Zalesky
5,403,797 A 4/1995 Ohtani et al.
5,411,889 A 5/1995 Hoots et al.
5,421,812 A 6/1995 Langley et al.
5,427,988 A 6/1995 Sengupta et al.
5,433,710 A 7/1995 VanAntwerp et al.
5,452,033 A 9/1995 Balling et al.
5,456,945 A 10/1995 McMillan et al.
5,468,727 A 11/1995 Phillips et al.
5,478,610 A 12/1995 Desu et al.
5,505,709 A 4/1996 Funderburk et al.
5,505,828 A 4/1996 Wong et al.
5,507,288 A 4/1996 Bocker et al.
5,513,382 A 4/1996 Agahi-Kesheh et al.
5,533,389 A 7/1996 Kamen et al.
5,535,445 A 7/1996 Gunton
5,540,772 A 7/1996 McMillan et al.
5,543,773 A 8/1996 Evans et al.
5,558,640 A 9/1996 Pfeiler et al.
5,563,584 A 10/1996 Rader et al.
5,569,186 A 10/1996 Lord et al.
5,576,781 A 11/1996 Deleeuw
5,582,593 A 12/1996 Hultman
5,584,053 A 12/1996 Kommrusch et al.
5,584,813 A 12/1996 Livingston et al.
5,585,733 A 12/1996 Paglione
5,586,553 A 12/1996 Halili et al.
5,590,387 A 12/1996 Schmidt et al.
5,609,572 A 3/1997 Lang
5,614,252 A 3/1997 McMillan et al.
5,625,365 A 4/1997 Tom et al.
5,635,433 A 6/1997 Sengupta
5,637,095 A 6/1997 Nason et al.
5,647,853 A 7/1997 Feldmann et al.
5,660,163 A 8/1997 Schulman et al.
5,665,065 A 9/1997 Colman et al.
5,665,070 A 9/1997 McPhee
5,678,539 A 10/1997 Schubert et al.
5,685,844 A 11/1997 Marttila
5,685,859 A 11/1997 Kornerup
5,693,018 A 12/1997 Kriesel et al.
5,697,899 A 12/1997 Hillman et al.
5,700,695 A 12/1997 Yassinzadeh et al.
5,703,364 A 12/1997 Rosenthal
5,707,459 A 1/1998 Itoyama et al.
5,707,715 A 1/1998 deRochemont et al.
5,713,875 A 2/1998 Tanner, II
5,714,123 A 2/1998 Sohrab
5,716,343 A 2/1998 Kriesel et al.
5,722,397 A 3/1998 Eppstein
5,726,404 A 3/1998 Brody
5,726,751 A 3/1998 Altendorf et al.
5,741,228 A 4/1998 Lambrecht et al.
5,746,217 A 5/1998 Erickson et al.
5,747,350 A 5/1998 Sattler
5,747,870 A 5/1998 Pedder
5,748,827 A 5/1998 Holl et al.
5,755,682 A 5/1998 Knudson et al.
5,758,643 A 6/1998 Wong et al.
5,759,923 A 6/1998 McMillan et al.
5,764,189 A 6/1998 Lohninger
5,771,567 A 6/1998 Pierce et al.
5,776,103 A 7/1998 Kriesel et al.
5,779,676 A 7/1998 Kriesel et al.
5,785,681 A 7/1998 Indravudh et al.
5,785,688 A 7/1998 Joshi et al.
5,797,881 A 8/1998 Gadot
5,800,397 A 9/1998 Wilson et al.
5,800,405 A 9/1998 McPhee
5,800,420 A 9/1998 Gross et al.
5,801,057 A 9/1998 Smart et al.
5,804,048 A 9/1998 Wong et al.
5,807,075 A 9/1998 Jacobsen et al.
5,817,007 A 10/1998 Fodgaard et al.
5,820,622 A 10/1998 Gross et al.
5,823,951 A 10/1998 Messerschmidt
5,830,999 A 11/1998 Dunn
5,839,467 A 11/1998 Saaski et al.
5,840,020 A 11/1998 Heinonen et al.
5,848,991 A 12/1998 Gross et al.
5,851,197 A 12/1998 Marano et al.
5,854,608 A 12/1998 Leisten
5,858,005 A 1/1999 Kriesel
5,858,239 A 1/1999 Kenley et al.
5,859,621 A 1/1999 Leisten
5,865,806 A 2/1999 Howell
5,867,688 A 2/1999 Simmon et al.
5,871,470 A 2/1999 McWha
5,879,310 A 3/1999 Sopp et al.
5,889,459 A 3/1999 Hattori et al.
5,891,097 A 4/1999 Saito et al.
5,892,489 A 4/1999 Kanba et al.
5,897,530 A 4/1999 Jackson
5,899,882 A 5/1999 Waksman et al.
5,902,253 A 5/1999 Pfeiffer et al.
5,903,421 A 5/1999 Furutani et al.
5,906,597 A 5/1999 McPhee
5,911,716 A 6/1999 Rake et al.
5,919,167 A 7/1999 Mulhauser et al.
5,931,814 A 8/1999 Alex et al.
5,932,175 A 8/1999 Knute et al.
5,933,121 A 8/1999 Rainhart et al.
5,935,099 A 8/1999 Peterson et al.
5,945,963 A 8/1999 Leisten
5,947,911 A 9/1999 Wong et al.
5,957,890 A 9/1999 Mann et al.
5,961,492 A 10/1999 Kriesel et al.
5,965,848 A 10/1999 Altschul et al.
5,971,941 A 10/1999 Simons et al.
5,993,423 A 11/1999 Choi
5,997,501 A 12/1999 Gross et al.
6,017,318 A 1/2000 Gauthier et al.
6,019,747 A 2/2000 McPhee
6,023,251 A 2/2000 Koo et al.
6,024,539 A 2/2000 Blomquist
6,027,826 A 2/2000 deRochemont et al.
6,028,568 A 2/2000 Asakura et al.
6,031,445 A 2/2000 Marty et al.
6,032,059 A 2/2000 Henning et al.
6,036,924 A 3/2000 Simons et al.
6,040,578 A 3/2000 Malin et al.
6,040,805 A 3/2000 Huynh et al.
6,046,707 A 4/2000 Gaughan et al.
6,049,727 A 4/2000 Crothall
6,050,978 A 4/2000 Orr et al.
6,052,040 A 4/2000 Hino
6,058,934 A 5/2000 Sullivan
6,066,103 A 5/2000 Duchon et al.
6,071,292 A 6/2000 Makower et al.
6,072,180 A 6/2000 Kramer et al.
6,077,055 A 6/2000 Vilks
6,090,092 A 7/2000 Fowles et al.
6,101,406 A 8/2000 Hacker et al.
6,102,872 A 8/2000 Doneen et al.
6,111,544 A 8/2000 Dakeya et al.
6,115,673 A 9/2000 Malin et al.
6,123,827 A 9/2000 Wong et al.
6,124,134 A 9/2000 Stark
6,126,637 A 10/2000 Kriesel et al.
6,128,519 A 10/2000 Say
6,142,939 A 11/2000 Eppstein et al.
6,143,164 A 11/2000 Heller et al.
6,143,432 A 11/2000 de Rochemont et al.
6,154,176 A 11/2000 Fathy et al.
6,157,041 A 12/2000 Thomas et al.
6,161,028 A 12/2000 Braig et al.
6,162,639 A 12/2000 Douglas
6,171,264 B1 1/2001 Bader
6,174,300 B1 1/2001 Kriesel et al.
6,176,004 B1 1/2001 Rainhart et al.
6,181,297 B1 1/2001 Leisten
6,188,368 B1 2/2001 Koriyama et al.
6,190,359 B1 2/2001 Heruth
6,195,049 B1 2/2001 Kim et al.

(56) References Cited

U.S. PATENT DOCUMENTS 6,196,046 B1 3/2001 Braig et al.
6,200,287 B1 3/2001 Keller et al.
6,200,293 B1 3/2001 Kriesel et al.
6,200,338 B1 3/2001 Solomon et al.
6,204,203 B1 3/2001 Narwankar et al.
6,208,843 B1 3/2001 Huang et al.
6,214,629 B1 4/2001 Freitag et al.
6,222,489 B1 4/2001 Tsuru et al.
6,226,082 B1 5/2001 Roe
6,244,776 B1 6/2001 Wiley
6,261,065 B1 7/2001 Nayak et al.
6,262,798 B1 7/2001 Shepherd et al.
6,266,020 B1 7/2001 Chang
6,270,455 B1 8/2001 Brown
6,271,045 B1 8/2001 Douglas et al.
6,280,381 B1 8/2001 Malin et al.
6,285,448 B1 9/2001 Kuenstner
6,300,894 B1 10/2001 Lynch et al.
6,309,370 B1 10/2001 Haim et al.
6,312,888 B1 11/2001 Wong et al.
6,320,547 B1 11/2001 Fathy et al.
6,323,549 B1 11/2001 deRochemont et al.
6,334,851 B1 1/2002 Hayes et al.
6,363,609 B1 4/2002 Pickren
6,375,627 B1 4/2002 Mauze et al.
6,375,638 B2 4/2002 Nason et al.
6,379,301 B1 4/2002 Worthington et al.
6,381,029 B1 4/2002 Tipirneni
6,399,745 B1 6/2002 Ertl
6,402,689 B1 6/2002 Scarantino et al.
6,468,242 B1 10/2002 Wilson
6,470,279 B1 10/2002 Samsoondar
6,474,219 B2 11/2002 Klitmose et al.
6,475,196 B1 11/2002 Vachon
6,477,065 B2 11/2002 Parks
6,477,901 B1 11/2002 Tadigadapa et al.
6,484,044 B1 11/2002 Lilienfeld-Toal
6,485,461 B1 11/2002 Mason et al.
6,485,462 B1 11/2002 Kriesel
6,491,656 B1 12/2002 Morris
6,492,949 B1 12/2002 Breglia et al.
6,496,149 B1 12/2002 Birnbaum et al.
6,501,415 B1 12/2002 Viana et al.
6,512,937 B2 1/2003 Blank et al.
6,520,936 B1 2/2003 Mann
6,525,509 B1 2/2003 Petersson et al.
6,527,744 B1 3/2003 Kriesel et al.
6,528,809 B1 3/2003 Thomas et al.
6,537,249 B2 3/2003 Kriesell et al.
6,540,260 B1 4/2003 Tan
6,540,672 B1 4/2003 Simonsen et al.
6,541,820 B1 4/2003 Bol
6,544,212 B2 4/2003 Galley et al.
6,546,268 B1 4/2003 Ishikawa et al.
6,546,269 B1 4/2003 Kurnik
6,552,693 B1 4/2003 Leisten
6,553,841 B1 4/2003 Blouch
6,554,798 B1 4/2003 Mann et al.
6,556,850 B1 4/2003 Braig et al.
6,558,351 B1 5/2003 Steil et al.
6,559,735 B1 5/2003 Hoang et al.
6,560,471 B1 5/2003 Heller et al.
6,561,978 B1 5/2003 Conn et al.
6,562,001 B2 5/2003 Lebel et al.
6,562,014 B2 5/2003 Lin et al.
6,569,115 B1 5/2003 Barker et al.
6,569,125 B2 5/2003 Jepson et al.
6,572,542 B1 6/2003 Houben et al.
6,572,545 B2 6/2003 Knobbe et al.
6,574,490 B2 6/2003 Abbink et al.
6,575,905 B2 6/2003 Knobbe et al.
6,580,934 B1 6/2003 Braig et al.
6,583,699 B2 6/2003 Yokoyama
6,595,956 B1 7/2003 Gross et al.
6,605,151 B1 8/2003 Wessels et al.
6,611,419 B1 8/2003 Chakravorty
6,618,603 B2 9/2003 Varalli et al.
6,620,750 B2 9/2003 Kim et al.
6,633,772 B2 10/2003 Ford et al.
6,635,958 B2 10/2003 Bates et al.
6,639,556 B2 10/2003 Baba
6,642,908 B2 11/2003 Pleva et al.
6,645,142 B2 11/2003 Braig et al.
6,650,303 B2 11/2003 Kim et al.
6,653,091 B1 11/2003 Dunn et al.
6,656,158 B2 12/2003 Mahoney et al.
6,662,030 B2 12/2003 Khalil et al.
6,669,663 B1 12/2003 Thompson
6,670,497 B2 12/2003 Tashino et al.
6,678,542 B2 1/2004 Braig et al.
6,680,700 B2 1/2004 Hilgers
6,683,576 B2 1/2004 Achim
6,685,452 B2 2/2004 Christiansen et al.
6,686,406 B2 2/2004 Tomomatsu et al.
6,690,336 B1 2/2004 Leisten et al.
6,697,605 B1 2/2004 Atokawa et al.
6,699,218 B2 3/2004 Flaherty et al.
6,699,221 B2 3/2004 Vaillancourt
6,718,189 B2 4/2004 Rohrscheib et al.
6,720,926 B2 4/2004 Killen et al.
6,721,582 B2 4/2004 Trepagnier et al.
6,723,072 B2 4/2004 Flaherty et al.
6,727,785 B2 4/2004 Killen et al.
6,728,560 B2 4/2004 Kollias et al.
6,731,244 B2 5/2004 Killen et al.
6,731,248 B2 5/2004 Killen et al.
6,733,890 B2 5/2004 Imanaka et al.
6,740,059 B2 5/2004 Flaherty
6,740,072 B2 5/2004 Starkweather et al.
6,741,148 B2 5/2004 Killen et al.
6,742,249 B2 6/2004 deRochemont et al.
6,743,744 B1 6/2004 Kim et al.
6,750,740 B2 6/2004 Killen et al.
6,750,820 B2 6/2004 Killen et al.
6,751,490 B2 6/2004 Esenaliev et al.
6,753,745 B2 6/2004 Killen et al.
6,753,814 B2 6/2004 Killen et al.
6,758,835 B2 7/2004 Close et al.
6,762,237 B2 7/2004 Glatkowski et al.
6,768,319 B2 7/2004 Wang
6,780,156 B2 8/2004 Haueter et al.
6,787,181 B2 9/2004 Uchiyama et al.
6,791,496 B1 9/2004 Killen et al.
6,810,290 B2 10/2004 Lebel et al.
6,826,031 B2 11/2004 Nagai et al.
6,830,558 B2 12/2004 Flaherty et al.
6,830,623 B2 12/2004 Hayashi et al.
6,837,858 B2 1/2005 Cunningham et al.
6,837,988 B2 1/2005 Leong et al.
6,846,288 B2 1/2005 Nagar et al.
6,853,288 B2 2/2005 Ahn et al.
6,858,892 B2 2/2005 Yamagata
6,862,534 B2 3/2005 Sterling et al.
6,864,848 B2 3/2005 Sievenpiper
6,865,408 B1 3/2005 Abbink et al.
6,871,396 B2 3/2005 Sugaya et al.
6,878,871 B2 4/2005 Scher et al.
6,883,778 B1 4/2005 Newton et al.
6,890,291 B2 5/2005 Robinson et al.
6,900,016 B1 5/2005 Venter
6,905,989 B2 6/2005 Ellis et al.
6,906,674 B2 6/2005 McKinzie, III et al.
6,914,566 B2 7/2005 Beard
6,919,119 B2 7/2005 Kalkan et al.
6,928,298 B2 8/2005 Furutani et al.
6,936,029 B2 8/2005 Mann et al.
6,943,430 B2 9/2005 Kwon
6,943,731 B2 9/2005 Killen et al.
6,949,081 B1 9/2005 Chance
6,958,809 B2 10/2005 Sterling et al.
6,963,259 B2 11/2005 Killen et al.
6,989,891 B2 1/2006 Braig et al.
6,990,366 B2 1/2006 Say et al.
7,002,436 B2 2/2006 Ma et al.

(56) References Cited

U.S. PATENT DOCUMENTS 7,008,404 B2 3/2006 Nakajima
7,009,180 B2 3/2006 Sterling et al.
7,016,713 B2 3/2006 Gardner et al.
7,018,360 B2 3/2006 Flaherty et al.
7,025,743 B2 4/2006 Mann et al.
7,025,744 B2 4/2006 Utterberg et al.
7,027,848 B2 4/2006 Robinson et al.
7,043,288 B2 5/2006 Davis, III et al.
7,047,637 B2 5/2006 deRochemont et al.
7,060,059 B2 6/2006 Keith et al.
7,060,350 B2 6/2006 Takaya et al.
7,061,593 B2 6/2006 Braig et al.
7,096,124 B2 8/2006 Sterling et al.
7,115,205 B2 10/2006 Robinson et al.
7,116,949 B2 10/2006 Irie et al.
7,128,727 B2 10/2006 Flaherty et al.
7,137,694 B2 11/2006 Ferran et al.
7,139,593 B2 11/2006 Kavak et al.
7,139,598 B2 11/2006 Hull et al.
7,144,384 B2 12/2006 Gorman et al.
7,160,272 B1 1/2007 Eyal et al.
7,171,252 B1 1/2007 Scarantino et al.
7,182,726 B2 2/2007 Williams et al.
7,190,988 B2 3/2007 Say et al.
7,204,823 B2 4/2007 Estes et al.
7,230,316 B2 6/2007 Yamazaki et al.
7,248,912 B2 7/2007 Gough et al.
7,267,665 B2 9/2007 Steil et al.
7,271,912 B2 9/2007 Sterling et al.
7,278,983 B2 10/2007 Ireland et al.
7,291,107 B2 11/2007 Hellwig et al.
7,291,497 B2 11/2007 Holmes et al.
7,291,782 B2 11/2007 Sager et al.
7,303,073 B2 12/2007 Raynal-Olive et al.
7,303,549 B2 12/2007 Flaherty et al.
7,303,622 B2 12/2007 Loch et al.
7,303,922 B2 12/2007 Jeng et al.
7,354,420 B2 4/2008 Steil et al.
7,388,202 B2 6/2008 Sterling et al.
7,402,153 B2 7/2008 Steil et al.
7,404,796 B2 7/2008 Ginsberg
7,405,698 B2 7/2008 de Rochemont
7,429,255 B2 9/2008 Thompson
7,460,130 B2 12/2008 Salganicoff
7,481,787 B2 1/2009 Gable et al.
7,491,187 B2 2/2009 Van Den Berghe et al.
7,500,949 B2 3/2009 Gottlieb et al.
7,509,156 B2 3/2009 Flanders
7,522,124 B2 4/2009 Smith et al.
7,547,281 B2 6/2009 Hayes et al.
7,553,512 B2 6/2009 Kodas et al.
7,564,887 B2 7/2009 Wang et al.
7,569,030 B2 8/2009 Lebel et al.
7,595,623 B2 9/2009 Bennett
7,608,042 B2 10/2009 Goldberger et al.
7,651,845 B2 1/2010 Doyle, III et al.
7,652,901 B2 1/2010 Kirchmeier et al.
7,680,529 B2 3/2010 Kroll
7,714,794 B2 5/2010 Tavassoli Hozouri
7,734,323 B2 6/2010 Blomquist et al.
7,763,917 B2 7/2010 de Rochemont
7,766,829 B2 8/2010 Sloan et al.
7,771,391 B2 8/2010 Carter
7,785,258 B2 8/2010 Braig et al.
7,806,854 B2 10/2010 Damiano et al.
7,806,886 B2 10/2010 Kanderian, Jr. et al.
7,812,774 B2 10/2010 Friman et al.
7,918,825 B2 4/2011 OConnor et al.
7,946,985 B2 5/2011 Mastrototaro et al.
7,972,296 B2 7/2011 Braig et al.
8,056,719 B2 11/2011 Porret et al.
8,066,805 B2 11/2011 Zurcher et al.
8,069,690 B2 12/2011 DeSantolo et al.
8,105,282 B2 1/2012 Susi et al.
8,114,489 B2 2/2012 Nemat-Nasser et al.
8,178,457 B2 5/2012 de Rochemont
8,193,873 B2 6/2012 Kato et al.
8,221,345 B2 7/2012 Blomquist
8,251,907 B2 8/2012 Sterling et al.
8,267,921 B2 9/2012 Yodfat et al.
8,285,487 B2 10/2012 Bergstrom et al.
8,350,657 B2 1/2013 deRochemont
8,354,294 B2 1/2013 de Rochemont et al.
8,449,524 B2 5/2013 Braig et al.
8,452,359 B2 5/2013 Rebec et al.
8,454,557 B1 6/2013 Qi et al.
8,454,576 B2 6/2013 Mastrototaro et al.
8,461,561 B2 6/2013 Freeman et al.
8,467,980 B2 6/2013 Campbell et al.
8,478,557 B2 7/2013 Hayter et al.
8,547,239 B2 10/2013 Peatfield et al.
8,593,819 B2 11/2013 de Rochemont
8,597,274 B2 12/2013 Sloan et al.
8,622,954 B2 1/2014 Shahmirian
8,622,988 B2 1/2014 Hayter
8,715,839 B2 5/2014 de Rochemont
8,727,117 B2 5/2014 Maasarani
8,810,394 B2 8/2014 Kalpin
8,818,782 B2 8/2014 Thukral et al.
8,920,628 B2 12/2014 Gerber
8,939,935 B2 1/2015 OConnor et al.
9,005,166 B2 4/2015 Uber, III et al.
9,061,097 B2 6/2015 Holt et al.
9,171,343 B1 10/2015 Fischell et al.
9,180,244 B2 11/2015 Anderson et al.
9,192,716 B2 11/2015 Jugl et al.
9,233,204 B2 1/2016 Booth et al.
9,248,229 B2 2/2016 Devouassoux et al.
9,402,950 B2 8/2016 Dilanni et al.
9,427,710 B2 8/2016 Jansen
9,486,571 B2 11/2016 Rosinko
9,520,649 B2 12/2016 de Rochemont
9,579,456 B2 2/2017 Budiman et al.
9,598,195 B2 3/2017 Deutschle et al.
9,656,017 B2 5/2017 Greene
9,743,224 B2 8/2017 San Vicente et al.
9,857,090 B2 1/2018 Golden et al.
9,862,519 B2 1/2018 Deutschle et al.
9,907,515 B2 3/2018 Doyle, III et al.
9,974,903 B1 5/2018 Davis et al.
9,980,140 B1 5/2018 Spencer et al.
9,984,773 B2 5/2018 Gondhalekar et al.
10,046,114 B1 8/2018 Biederman et al.
10,080,840 B2 9/2018 Gescheit et al.
10,086,131 B2 10/2018 Okihara
10,248,839 B2 4/2019 Levy et al.
10,335,464 B1 7/2019 Michelich et al.
10,342,926 B2 7/2019 Nazzaro et al.
10,441,717 B2 10/2019 Schmid et al.
10,583,250 B2 3/2020 Mazlish et al.
10,736,548 B2 8/2020 Ahmad et al.
10,737,024 B2 8/2020 Schmid
10,987,468 B2 4/2021 Mazlish et al.
11,197,964 B2 12/2021 Sjolund et al.
11,260,169 B2 3/2022 Estes
11,538,587 B2 12/2022 Bill
12,226,239 B2 2/2025 Williams
2001/0021803 A1 9/2001 Blank et al.
2001/0034023 A1 10/2001 Stanton, Jr. et al.
2001/0034502 A1 10/2001 Moberg et al.
2001/0048969 A1 12/2001 Constantino et al.
2001/0051377 A1 12/2001 Hammer et al.
2001/0053895 A1 12/2001 Vaillancourt
2001/0056258 A1 12/2001 Evans
2002/0010401 A1 1/2002 Bushmakin et al.
2002/0010423 A1 1/2002 Gross et al.
2002/0016568 A1 2/2002 Lebel et al.
2002/0032374 A1 3/2002 Holker et al.
2002/0040208 A1 4/2002 Flaherty et al.
2002/0047768 A1 4/2002 Duffy
2002/0070983 A1 6/2002 Kozub et al.
2002/0123740 A1 9/2002 Flaherty et al.
2002/0128543 A1 9/2002 Leonhardt
2002/0147423 A1 10/2002 Burbank et al.

(56) References Cited

U.S. PATENT DOCUMENTS

2002/0155425 A1 10/2002 Han et al.
2002/0161288 A1 10/2002 Shin et al.
2002/0161307 A1 10/2002 Yu et al.
2002/0173769 A1 11/2002 Gray et al.
2002/0190818 A1 12/2002 Endou et al.
2003/0023148 A1 1/2003 Lorenz et al.
2003/0034124 A1 2/2003 Sugaya et al.
2003/0040715 A1 2/2003 DAntonio et al.
2003/0050621 A1 3/2003 Lebel et al.
2003/0060692 A1 3/2003 Ruchti et al.
2003/0073952 A1 4/2003 Flaherty et al.
2003/0086074 A1 5/2003 Braig et al.
2003/0086075 A1 5/2003 Braig et al.
2003/0090649 A1 5/2003 Sterling et al.
2003/0100040 A1 5/2003 Bonnecaze et al.
2003/0122647 A1 7/2003 Ou
2003/0130616 A1 7/2003 Steil et al.
2003/0135388 A1 7/2003 Martucci et al.
2003/0144582 A1 7/2003 Cohen et al.
2003/0148024 A1 8/2003 Kodas et al.
2003/0163097 A1 8/2003 Fleury et al.
2003/0163789 A1 8/2003 Blomquist
2003/0170436 A1 9/2003 Sumi et al.
2003/0195404 A1 10/2003 Knobbe et al.
2003/0208113 A1 11/2003 Mault et al.
2003/0208154 A1 11/2003 Close et al.
2003/0212379 A1 11/2003 Bylund et al.
2003/0216627 A1 11/2003 Lorenz et al.
2003/0220605 A1 11/2003 Bowman, Jr. et al.
2003/0221621 A1 12/2003 Pokharna et al.
2004/0010207 A1 1/2004 Flaherty et al.
2004/0010507 A1 1/2004 Bellew
2004/0034295 A1 2/2004 Salganicoff
2004/0045879 A1 3/2004 Shults et al.
2004/0051368 A1 3/2004 Caputo et al.
2004/0064088 A1 4/2004 Gorman et al.
2004/0064259 A1 4/2004 Haaland et al.
2004/0068224 A1 4/2004 Alfred, Jr. et al.
2004/0069044 A1 4/2004 Lavi et al.
2004/0085215 A1 5/2004 Moberg et al.
2004/0097796 A1 5/2004 Berman et al.
2004/0116847 A1 6/2004 Wall
2004/0122353 A1 6/2004 Shahmirian et al.
2004/0133166 A1 7/2004 Moberg et al.
2004/0147034 A1 7/2004 Gore et al.
2004/0171983 A1 9/2004 Sparks et al.
2004/0203357 A1 10/2004 Nassimi
2004/0204868 A1 10/2004 Maynard et al.
2004/0215492 A1 10/2004 Choi
2004/0220517 A1 11/2004 Starkweather et al.
2004/0241736 A1 12/2004 Hendee et al.
2004/0249308 A1 12/2004 Forssell
2005/0003470 A1 1/2005 Nelson et al.
2005/0020980 A1 1/2005 Inoue et al.
2005/0022274 A1* 1/2005 Campbell .............. G16H 40/67
D24/100
2005/0033148 A1 2/2005 Haueter et al.
2005/0038680 A1 2/2005 McMahon
2005/0049179 A1 3/2005 Davidson et al.
2005/0055242 A1 3/2005 Bello et al.
2005/0065464 A1 3/2005 Talbot et al.
2005/0065465 A1 3/2005 Lebel et al.
2005/0075624 A1 4/2005 Miesel
2005/0105095 A1 5/2005 Pesach et al.
2005/0134609 A1 6/2005 Yu
2005/0137573 A1 6/2005 McLaughlin
2005/0171503 A1 8/2005 Van Den Berghe et al.
2005/0182306 A1 8/2005 Sloan
2005/0182366 A1 8/2005 Vogt et al.
2005/0192494 A1 9/2005 Ginsberg
2005/0192557 A1 9/2005 Brauker et al.
2005/0197621 A1 9/2005 Poulsen et al.
2005/0203360 A1 9/2005 Brauker et al.
2005/0203461 A1 9/2005 Flaherty et al.
2005/0238507 A1 10/2005 Dilanni et al.
2005/0261660 A1 11/2005 Choi
2005/0262451 A1 11/2005 Remignanti et al.
2005/0272640 A1 12/2005 Doyle, III et al.
2005/0277912 A1 12/2005 John
2006/0009727 A1 1/2006 OMahony et al.
2006/0041229 A1 2/2006 Garibotto et al.
2006/0079765 A1 4/2006 Neer et al.
2006/0079809 A1 4/2006 Goldberger et al.
2006/0086909 A1 4/2006 Schaber
2006/0086994 A1 4/2006 Viefers et al.
2006/0092569 A1 5/2006 Che et al.
2006/0100494 A1 5/2006 Kroll
2006/0134323 A1 6/2006 OBrien
2006/0134491 A1 6/2006 Hilchenko et al.
2006/0167350 A1 7/2006 Monfre et al.
2006/0173406 A1 8/2006 Hayes et al.
2006/0178633 A1 8/2006 Garibotto et al.
2006/0189925 A1 8/2006 Gable et al.
2006/0189926 A1 8/2006 Hall et al.
2006/0197015 A1 9/2006 Sterling et al.
2006/0200070 A1 9/2006 Callicoat et al.
2006/0204535 A1 9/2006 Johnson
2006/0229531 A1 10/2006 Goldberger et al.
2006/0253085 A1 11/2006 Geismar et al.
2006/0264895 A1 11/2006 Flanders
2006/0264926 A1 11/2006 Kochamba
2006/0270983 A1 11/2006 Lord et al.
2006/0276771 A1 12/2006 Galley et al.
2006/0282290 A1 12/2006 Flaherty et al.
2007/0016127 A1 1/2007 Staib et al.
2007/0027370 A1 2/2007 Brauker et al.
2007/0060796 A1 3/2007 Kim
2007/0060869 A1 3/2007 Tolle et al.
2007/0060872 A1 3/2007 Hall et al.
2007/0078784 A1 4/2007 Donovan et al.
2007/0083160 A1 4/2007 Hall et al.
2007/0100635 A1 5/2007 Mahajan et al.
2007/0106135 A1 5/2007 Sloan et al.
2007/0112298 A1* 5/2007 Mueller, Jr. ...... A61M 5/14244
600/316
2007/0116601 A1 5/2007 Patton
2007/0118405 A1* 5/2007 Campbell ......... A61M 5/14248
705/2
2007/0129690 A1 6/2007 Rosenblatt et al.
2007/0142720 A1 6/2007 Ridder et al.
2007/0166453 A1 7/2007 Van Duren et al.
2007/0173761 A1 7/2007 Kanderian et al.
2007/0173974 A1 7/2007 Lin et al.
2007/0179352 A1 8/2007 Randlov et al.
2007/0179885 A1 8/2007 Bird et al.
2007/0191702 A1* 8/2007 Yodfat ............... A61B 5/14546
600/347
2007/0191716 A1 8/2007 Goldberger et al.
2007/0191770 A1 8/2007 Moberg et al.
2007/0197163 A1 8/2007 Robertson
2007/0225675 A1 9/2007 Robinson et al.
2007/0233051 A1 10/2007 Hohl et al.
2007/0244381 A1 10/2007 Robinson et al.
2007/0249007 A1 10/2007 Rosero
2007/0259768 A1 11/2007 Kear et al.
2007/0264707 A1 11/2007 Liederman et al.
2007/0282269 A1 12/2007 Carter et al.
2007/0287985 A1 12/2007 Estes et al.
2007/0293843 A1 12/2007 Ireland et al.
2008/0004515 A1 1/2008 Jennewine
2008/0027371 A1 1/2008 Higuchi et al.
2008/0033272 A1 2/2008 Gough et al.
2008/0051738 A1 2/2008 Griffin
2008/0051764 A1 2/2008 Dent et al.
2008/0058625 A1 3/2008 McGarraugh et al.
2008/0065050 A1 3/2008 Sparks et al.
2008/0071157 A1 3/2008 McGarraugh et al.
2008/0071158 A1 3/2008 McGarraugh et al.
2008/0077081 A1 3/2008 Mounce et al.
2008/0078400 A1 4/2008 Martens et al.
2008/0097289 A1 4/2008 Steil et al.
2008/0114304 A1 5/2008 Nalesso et al.
2008/0132880 A1 6/2008 Buchman
2008/0160492 A1 7/2008 Campbell et al.

(56) References Cited

U.S. PATENT DOCUMENTS

2008/0161664 A1 7/2008 Mastrototaro et al.
2008/0172026 A1 7/2008 Blomquist
2008/0172028 A1 7/2008 Blomquist
2008/0172031 A1* 7/2008 Blomquist ............ G16H 20/17 604/500
2008/0173073 A1 7/2008 Downie et al.
2008/0177165 A1 7/2008 Blomquist et al.
2008/0188796 A1 8/2008 Steil et al.
2008/0200838 A1 8/2008 Goldberger et al.
2008/0206067 A1 8/2008 De Corral et al.
2008/0208113 A1 8/2008 Damiano et al.
2008/0214919 A1 9/2008 Harmon et al.
2008/0228056 A1 9/2008 Blomquist et al.
2008/0249386 A1 10/2008 Besterman et al.
2008/0255438 A1 10/2008 Saidara et al.
2008/0269585 A1 10/2008 Ginsberg
2008/0269714 A1 10/2008 Mastrototaro et al.
2008/0269723 A1 10/2008 Mastrototaro et al.
2008/0281290 A1 11/2008 Yodfat et al.
2008/0287906 A1 11/2008 Burkholz et al.
2009/0006061 A1 1/2009 Thukral et al.
2009/0018406 A1* 1/2009 Yodfat ................ A61M 5/1723 702/19
2009/0030398 A1* 1/2009 Yodfat .................. G16H 20/17 702/19
2009/0036753 A1 2/2009 King
2009/0043240 A1 2/2009 Robinson et al.
2009/0048556 A1 2/2009 Durand
2009/0054753 A1 2/2009 Robinson et al.
2009/0062767 A1 3/2009 Van Antwerp et al.
2009/0069743 A1 3/2009 Krishnamoorthy et al.
2009/0069745 A1 3/2009 Estes et al.
2009/0069787 A1 3/2009 Estes et al.
2009/0099521 A1 4/2009 Gravesen et al.
2009/0105573 A1 4/2009 Malecha
2009/0112769 A1 4/2009 Dicks et al.
2009/0131861 A1 5/2009 Braig et al.
2009/0143661 A1 6/2009 Taub
2009/0156922 A1 6/2009 Goldberger et al.
2009/0156924 A1 6/2009 Shariati et al.
2009/0163781 A1 6/2009 Say et al.
2009/0177142 A1 7/2009 Blomquist et al.
2009/0177147 A1* 7/2009 Blomquist .......... A61M 5/1723 702/19
2009/0198350 A1 8/2009 Thiele
2009/0221890 A1 9/2009 Saffer et al.
2009/0228214 A1 9/2009 Say et al.
2009/0254041 A1 10/2009 Krag et al.
2009/0318791 A1 12/2009 Kaastrup
2009/0326343 A1 12/2009 Gable et al.
2009/0326472 A1 12/2009 Carter
2010/0017141 A1 1/2010 Campbell et al.
2010/0036326 A1 2/2010 Matusch
2010/0057042 A1 3/2010 Hayter
2010/0064243 A1 3/2010 Buck et al.
2010/0076275 A1 3/2010 Chu et al.
2010/0077198 A1 3/2010 Buck et al.
2010/0094251 A1 4/2010 Estes
2010/0114026 A1 5/2010 Karratt et al.
2010/0121170 A1 5/2010 Rule
2010/0137784 A1 6/2010 Cefai et al.
2010/0145272 A1 6/2010 Cefai et al.
2010/0152658 A1 6/2010 Hanson et al.
2010/0174228 A1 7/2010 Buckingham et al.
2010/0185175 A1* 7/2010 Kamen ................ G05D 7/0647 604/67
2010/0185183 A1 7/2010 Alme et al.
2010/0211003 A1 8/2010 Sundar et al.
2010/0228110 A1 9/2010 Tsoukalis
2010/0241066 A1 9/2010 Hansen et al.
2010/0262117 A1 10/2010 Magni et al.
2010/0262434 A1 10/2010 Shaya
2010/0286997 A1 11/2010 Srinivasan
2010/0295686 A1 11/2010 Sloan et al.
2010/0298765 A1 11/2010 Budiman et al.
2011/0021584 A1 1/2011 Berggren et al.
2011/0028817 A1 2/2011 Jin et al.
2011/0049394 A1 3/2011 de Rochemont
2011/0054390 A1 3/2011 Searle et al.
2011/0054399 A1 3/2011 Chong et al.
2011/0065224 A1 3/2011 Bollman et al.
2011/0071765 A1 3/2011 Yodfat et al.
2011/0124996 A1 5/2011 Reinke et al.
2011/0142688 A1 6/2011 Chappel et al.
2011/0144586 A1 6/2011 Michaud et al.
2011/0152658 A1 6/2011 Peyser et al.
2011/0160652 A1 6/2011 Yodfat et al.
2011/0178472 A1 7/2011 Cabiri
2011/0190694 A1 8/2011 Lanier, Jr. et al.
2011/0202005 A1 8/2011 Yodfat et al.
2011/0213306 A1 9/2011 Hanson et al.
2011/0218495 A1 9/2011 Remebe
2011/0225024 A1 9/2011 Seyer et al.
2011/0230833 A1 9/2011 Landman et al.
2011/0246235 A1 10/2011 Powell et al.
2011/0251509 A1 10/2011 Beyhan et al.
2011/0257496 A1 10/2011 Terashima
2011/0313680 A1 12/2011 Doyle, III
2011/0316562 A1 12/2011 Cefai et al.
2012/0003935 A1 1/2012 Lydon et al.
2012/0010594 A1 1/2012 Holt et al.
2012/0029941 A1 2/2012 Malave et al.
2012/0030393 A1 2/2012 Ganesh et al.
2012/0050046 A1 3/2012 Satorius et al.
2012/0053556 A1 3/2012 Lee
2012/0054841 A1 3/2012 Schultz et al.
2012/0078067 A1 3/2012 Kovatchev et al.
2012/0078161 A1 3/2012 Masterson et al.
2012/0078181 A1 3/2012 Smith et al.
2012/0101451 A1 4/2012 Boit et al.
2012/0123234 A1* 5/2012 Atlas ................... A61B 5/7264 600/365
2012/0124521 A1 5/2012 Guo
2012/0136336 A1 5/2012 Mastrototaro et al.
2012/0150446 A1 6/2012 Chang et al.
2012/0153936 A1 6/2012 Romani et al.
2012/0172833 A1* 7/2012 Zisapel .............. A61M 5/1723 604/503
2012/0182939 A1 7/2012 Rajan et al.
2012/0184909 A1 7/2012 Gyrn
2012/0190955 A1 7/2012 Rao et al.
2012/0203085 A1 8/2012 Rebec
2012/0203178 A1 8/2012 Tverskoy
2012/0215087 A1 8/2012 Cobelli et al.
2012/0219935 A1 8/2012 Stebbings
2012/0225134 A1 9/2012 Komorowski
2012/0226259 A1 9/2012 Yodfat et al.
2012/0232520 A1 9/2012 Sloan et al.
2012/0238851 A1 9/2012 Kamen et al.
2012/0250449 A1 10/2012 Nakano
2012/0265166 A1 10/2012 Yodfat
2012/0271655 A1 10/2012 Knobel et al.
2012/0277667 A1 11/2012 Yodat et al.
2012/0277668 A1 11/2012 Chawla
2012/0282111 A1 11/2012 Nip et al.
2012/0295550 A1 11/2012 Wilson et al.
2013/0030358 A1 1/2013 Yodfat et al.
2013/0030841 A1 1/2013 Bergstrom et al.
2013/0036100 A1 2/2013 Nagpal et al.
2013/0060194 A1 3/2013 Rostein
2013/0080832 A1 3/2013 Dean et al.
2013/0138452 A1 5/2013 Cork et al.
2013/0158503 A1 6/2013 Kanderian, Jr. et al.
2013/0172695 A1 7/2013 Nielsen et al.
2013/0172710 A1 7/2013 Mears et al.
2013/0173473 A1 7/2013 Birtwhistle et al.
2013/0178791 A1 7/2013 Javitt
2013/0231642 A1 9/2013 Doyle et al.
2013/0245545 A1 9/2013 Arnold et al.
2013/0253472 A1 9/2013 Cabiri
2013/0261406 A1 10/2013 Rebec et al.
2013/0274576 A1 10/2013 Amirouche et al.
2013/0296792 A1 11/2013 Cabiri

(56) References Cited

U.S. PATENT DOCUMENTS

2013/0296823 A1 11/2013 Melker et al.
2013/0298080 A1 11/2013 Griffin et al.
2013/0317753 A1 11/2013 Kamen et al.
2013/0332874 A1 12/2013 Rosinko et al.
2013/0338576 A1 12/2013 OConnor et al.
2013/0346858 A1 12/2013 Neyrinck
2014/0005633 A1 1/2014 Finan
2014/0018730 A1 1/2014 Muller-Pathle
2014/0032549 A1 1/2014 McDaniel et al.
2014/0066886 A1 3/2014 Roy et al.
2014/0066887 A1 3/2014 Mastrototaro et al.
2014/0074033 A1 3/2014 Sonderegger et al.
2014/0074059 A1* 3/2014 Howell ............. A61M 5/14244 604/503
2014/0088428 A1 3/2014 Yang et al.
2014/0108046 A1 4/2014 Cabrera et al.
2014/0114277 A1 4/2014 Eggert et al.
2014/0121635 A1 5/2014 Hayter
2014/0128839 A1 5/2014 Dilanni et al.
2014/0129951 A1 5/2014 Amin et al.
2014/0135880 A1 5/2014 Baumgartner et al.
2014/0142508 A1 5/2014 Dilanni et al.
2014/0146202 A1 5/2014 Boss et al.
2014/0163664 A1 6/2014 Goldsmith
2014/0171901 A1 6/2014 Langsdorf et al.
2014/0180203 A1 6/2014 Budiman et al.
2014/0180240 A1 6/2014 Finan et al.
2014/0200426 A1 7/2014 Taub et al.
2014/0200559 A1 7/2014 Doyle et al.
2014/0230021 A1 8/2014 Birthwhistle et al.
2014/0276554 A1 9/2014 Finan et al.
2014/0276556 A1 9/2014 Saint et al.
2014/0278123 A1 9/2014 Prodhom et al.
2014/0309615 A1 10/2014 Mazlish
2014/0316379 A1 10/2014 Sonderegger et al.
2014/0325065 A1 10/2014 Birtwhistle et al.
2015/0018633 A1 1/2015 Kovachev et al.
2015/0025329 A1 1/2015 Amarasingham et al.
2015/0025495 A1 1/2015 Peyser
2015/0025503 A1 1/2015 Searle et al.
2015/0038898 A1 2/2015 Palmer et al.
2015/0041498 A1 2/2015 Kakiuchi et al.
2015/0057913 A1 2/2015 Benhammou
2015/0119666 A1 4/2015 Brister et al.
2015/0120317 A1 4/2015 Mayou et al.
2015/0134265 A1 5/2015 Kohlbrecher et al.
2015/0134353 A1 5/2015 Ferrell et al.
2015/0151050 A1* 6/2015 Estes ..................... A61M 5/172 604/151
2015/0165119 A1 6/2015 Palerm et al.
2015/0173674 A1 6/2015 Hayes et al.
2015/0193585 A1 7/2015 Sunna
2015/0202386 A1 7/2015 Brady et al.
2015/0205509 A1 7/2015 Scriven et al.
2015/0205511 A1 7/2015 Vinna et al.
2015/0213217 A1 7/2015 Amarasingham et al.
2015/0217046 A1* 8/2015 Heller ..................... A61P 25/16 514/486
2015/0217052 A1 8/2015 Keenan et al.
2015/0217053 A1 8/2015 Booth et al.
2015/0265767 A1 9/2015 Vazquez et al.
2015/0290391 A1 10/2015 Schmid et al.
2015/0301691 A1 10/2015 Qin
2015/0306314 A1 10/2015 Doyle et al.
2015/0331995 A1 11/2015 Zhao et al.
2015/0351671 A1 12/2015 Vanslyke et al.
2015/0352280 A1 12/2015 Deratany
2015/0356250 A1 12/2015 Polimeni
2015/0366945 A1 12/2015 Greene
2016/0015891 A1 1/2016 Papiorek
2016/0019352 A1 1/2016 Cohen et al.
2016/0022905 A1 1/2016 Nagar et al.
2016/0038673 A1 2/2016 Morales
2016/0038689 A1 2/2016 Lee et al.
2016/0051749 A1 2/2016 Istoc
2016/0082187 A1 3/2016 Schaible et al.
2016/0089494 A1 3/2016 Guerrini
2016/0175520 A1 6/2016 Palerm et al.
2016/0184517 A1 6/2016 Baek et al.
2016/0220181 A1 8/2016 Rigooard et al.
2016/0228641 A1 8/2016 Gescheit et al.
2016/0243318 A1 8/2016 Despa et al.
2016/0256087 A1 9/2016 Doyle et al.
2016/0259889 A1 9/2016 Murtha et al.
2016/0287512 A1 10/2016 Cooper et al.
2016/0302054 A1 10/2016 Kimura et al.
2016/0331310 A1 11/2016 Kovatchev
2016/0339172 A1 11/2016 Michaud et al.
2016/0354543 A1 12/2016 Cinar et al.
2017/0021096 A1 1/2017 Cole et al.
2017/0049386 A1 2/2017 Abraham et al.
2017/0053552 A1* 2/2017 Zhong .................. A61B 5/7405
2017/0131887 A1 5/2017 Kim et al.
2017/0143899 A1 5/2017 Gondhalekar et al.
2017/0143900 A1 5/2017 Rioux et al.
2017/0156682 A1 6/2017 Doyle et al.
2017/0173261 A1 6/2017 O'Connor et al.
2017/0189625 A1 7/2017 Cirillo et al.
2017/0213002 A1* 7/2017 Jha ...................... A61M 5/1723
2017/0216524 A1 8/2017 Haider et al.
2017/0239415 A1 8/2017 Hwang et al.
2017/0281877 A1 10/2017 Marlin et al.
2017/0296746 A1 10/2017 Chen et al.
2017/0311903 A1 11/2017 Davis et al.
2017/0332951 A1 11/2017 Ahmad
2017/0348482 A1 12/2017 Duke et al.
2018/0014113 A1 1/2018 Boesen
2018/0036495 A1 2/2018 Searle et al.
2018/0040255 A1 2/2018 Freeman et al.
2018/0075200 A1 3/2018 Davis et al.
2018/0075201 A1 3/2018 Davis et al.
2018/0075202 A1 3/2018 Davis et al.
2018/0092576 A1 4/2018 O'Connor et al.
2018/0126073 A1 5/2018 Wu et al.
2018/0169334 A1 6/2018 Grosman et al.
2018/0200434 A1 7/2018 Mazlish et al.
2018/0200438 A1 7/2018 Mazlish et al.
2018/0200441 A1 7/2018 Desborough et al.
2018/0204636 A1 7/2018 Edwards et al.
2018/0277246 A1 9/2018 Zhong
2018/0277253 A1 9/2018 Gondhalekar et al.
2018/0280609 A1 10/2018 Nishimura et al.
2018/0289891 A1 10/2018 Finan et al.
2018/0296757 A1 10/2018 Finan et al.
2018/0307515 A1 10/2018 Meller et al.
2018/0342317 A1 11/2018 Skirble et al.
2018/0369479 A1 12/2018 Hayter et al.
2019/0076600 A1 3/2019 Grosman et al.
2019/0095052 A1 3/2019 De Wever et al.
2019/0132801 A1 5/2019 Kamath et al.
2019/0184091 A1 6/2019 Sjolund et al.
2019/0240403 A1 8/2019 Palerm et al.
2019/0290844 A1 9/2019 Monirabbasi et al.
2019/0321545 A1 10/2019 Saint
2019/0336683 A1* 11/2019 O'Connor ........... A61M 5/1723
2019/0336684 A1 11/2019 O'Connor et al.
2019/0348157 A1 11/2019 Booth et al.
2019/0374714 A1 12/2019 Rioux et al.
2020/0001006 A1 1/2020 Pizzochero et al.
2020/0046268 A1 2/2020 Patek et al.
2020/0101222 A1 4/2020 Lintereur et al.
2020/0101223 A1 4/2020 Lintereur et al.
2020/0101225 A1 4/2020 O'Connor et al.
2020/0101286 A1 4/2020 Windmiller
2020/0113515 A1 4/2020 O'Connor et al.
2020/0219625 A1 7/2020 Kahlbaugh
2020/0342974 A1 10/2020 Chen et al.
2021/0050085 A1 2/2021 Hayter et al.
2021/0098105 A1 4/2021 Lee et al.
2021/0225480 A1 7/2021 Desborough
2022/0023536 A1 1/2022 Graham et al.
2022/0273872 A1* 9/2022 Narayanaswami .... A61B 5/024
2023/0128193 A1 4/2023 Williams
2023/0338652 A1 10/2023 Narayanaswam i

(56) References Cited

U.S. PATENT DOCUMENTS

2023/0343430 A1* 10/2023 Narayanaswami .... G16H 50/30
2024/0099612 A1 3/2024 Budiman
2024/0206772 A1 6/2024 Hayter
2024/0306949 A1 9/2024 Kumar
2025/0255560 A1 8/2025 Williams

FOREIGN PATENT DOCUMENTS

CA 2863379 A1 8/2013
CN 1297140 A 5/2001
CN 101208699 A 6/2008
CN 201134101 Y 10/2008
DE 4200595 A1 7/1993
DE 19756872 A1 7/1999
EP 0026056 A1 4/1981
EP 0341049 A2 11/1989
EP 0496305 A2 7/1992
EP 0549341 A1 6/1993
EP 0867196 A2 9/1998
EP 0939451 A1 9/1999
EP 1177802 A1 2/2002
EP 1376759 A2 1/2004
EP 1491144 A1 12/2004
EP 0801578 B1 7/2006
EP 1762263 A1 3/2007
EP 1839694 A1 10/2007
EP 1852703 A1 11/2007
EP 2099384 A1 9/2009
EP 2139382 A1 1/2010
EP 2353628 A2 8/2011
EP 2397181 A1 12/2011
EP 2468338 A1 6/2012
EP 2666520 A1 11/2013
EP 2695573 A2 2/2014
EP 2703024 A1 3/2014
EP 1874390 B1 10/2014
EP 2830499 A1 2/2015
EP 2943149 A1 11/2015
EP 3068290 A1 9/2016
EP 3177344 A1 6/2017
EP 3187201 A1 7/2017
EP 3193979 A1 7/2017
EP 3314548 A1 5/2018
EP 1571582 B1 4/2019
EP 2897071 B1 5/2019
EP 3598942 A1 1/2020
EP 3607985 A1 2/2020
ES 2559866 T3 2/2016
FR 2096275 A5 2/1972
GB 1125897 A 9/1968
GB 1401588 A 7/1975
GB 2176595 A 12/1986
GB 2443260 A 4/2008
GB 2443261 A 4/2008
GB 2461086 A 12/2009
GB 2495014 A 3/2013
GB 2524717 A 10/2015
GB 2525149 A 10/2015
JP 51125993 A 11/1976
JP 02131777 A 5/1990
JP 2001190659 A 7/2001
JP 2003154190 A 5/2003
JP 2005326943 A 11/2005
JP 2007144141 A1 6/2007
JP 2004283378 A 10/2007
JP 2007307359 A 11/2007
JP 2008513142 A 5/2008
JP 2008242502 A 10/2008
JP 2012210441 A 11/2012
JP 2017525451 A 9/2017
JP 2018153569 A 10/2018
JP 2019525276 A 9/2019
TW 200740148 A 10/2007
TW M452390 U 5/2013
WO 200048112 A2 9/1968
WO 8606796 A1 11/1986
WO 9800193 A1 1/1998
WO 9801071 A1 1/1998
WO 9819145 A1 5/1998
WO 9824495 A1 6/1998
WO 9841267 A1 9/1998
WO 9855073 A1 12/1998
WO 9910040 A1 3/1999
WO 9910049 A1 3/1999
WO 9956803 A1 11/1999
WO 9962576 A1 12/1999
WO 0010628 A2 3/2000
WO 0013580 A1 3/2000
WO 0019887 A1 4/2000
WO 0030705 A1 6/2000
WO 200032258 A1 6/2000
WO 0061215 A1 10/2000
WO 0078210 A1 12/2000
WO 0172354 A2 10/2001
WO 2001078812 A1 10/2001
WO 2002015954 A1 2/2002
WO 0226282 A2 4/2002
WO 2002043866 A2 6/2002
WO 2002076535 A1 10/2002
WO 2002082990 A1 10/2002
WO 2003016882 A1 2/2003
WO 2003039362 A1 5/2003
WO 2003045233 A1 6/2003
WO 2003097133 A1 11/2003
WO 2004043250 A1 5/2004
WO 2005110601 A1 5/2004
WO 2004092715 A1 10/2004
WO 2005031631 A2 4/2005
WO 2005051170 A2 6/2005
WO 2005082436 A1 9/2005
WO 2005113036 A1 12/2005
WO 2006053007 A2 5/2006
WO 2006060668 A2 6/2006
WO 2007064835 A2 6/2007
WO 2007066152 A2 6/2007
WO 2007078937 A1 7/2007
WO 2007112034 A2 10/2007
WO 2008024810 A2 2/2008
WO 2008024814 A2 2/2008
WO 2008029403 A1 3/2008
WO 2008133702 A1 11/2008
WO 2009023634 A2 2/2009
WO 2009032399 A1 3/2009
WO 2009039203 A2 3/2009
WO 2009045462 A1 4/2009
WO 2009049252 A1 4/2009
WO 2009066287 A3 5/2009
WO 2009066288 A1 5/2009
WO 2009098648 A2 8/2009
WO 2009134380 A2 11/2009
WO 2010022069 A2 2/2010
WO 2010025433 A1 3/2010
WO 2010053702 A1 5/2010
WO 2010077279 A1 7/2010
WO 2010078434 A2 7/2010
WO 2010132077 A1 11/2010
WO 2010138848 A1 12/2010
WO 2010139793 A1 12/2010
WO 2010146579 A1 12/2010
WO 2010147659 A2 12/2010
WO 2011012465 A1 2/2011
WO 2011031458 A1 3/2011
WO 2011075042 A1 6/2011
WO 2011095483 A1 8/2011
WO 2011133823 A1 10/2011
WO 2012045667 A2 4/2012
WO 2012073032 A1 6/2012
WO 2012108959 A1 8/2012
WO 2012134588 A1 10/2012
WO 2012177353 A1 12/2012
WO 2012178134 A2 12/2012
WO 2013050535 A2 4/2013
WO 2013078200 A1 5/2013
WO 2013134486 A2 9/2013

(56) References Cited

FOREIGN PATENT DOCUMENTS

| | | | |
|---|---|---|---|
| WO | 2013149186 | A1 | 10/2013 |
| WO | 20130149186 | A1 | 10/2013 |
| WO | 2013177565 | A1 | 11/2013 |
| WO | 2013182321 | A1 | 12/2013 |
| WO | 2014029416 | A1 | 2/2014 |
| WO | 2014109898 | A1 | 7/2014 |
| WO | 2014110538 | A1 | 7/2014 |
| WO | 2014136105 | A1 | 9/2014 |
| WO | 2014149357 | A1 | 9/2014 |
| WO | 2014179774 | A1 | 11/2014 |
| WO | 2014194183 | A2 | 12/2014 |
| WO | 2015056259 | A1 | 4/2015 |
| WO | 2015061493 | A1 | 4/2015 |
| WO | 2015073211 | A1 | 5/2015 |
| WO | 2015081337 | A2 | 6/2015 |
| WO | 2015117082 | A1 | 8/2015 |
| WO | 2015117854 | A1 | 8/2015 |
| WO | 2015167201 | A1 | 11/2015 |
| WO | 2015177082 | A1 | 11/2015 |
| WO | 2015187366 | A1 | 12/2015 |
| WO | 2015187793 | A1 | 12/2015 |
| WO | 2016004088 | A1 | 1/2016 |
| WO | 2016022650 | A1 | 2/2016 |
| WO | 2016041873 | A1 | 3/2016 |
| WO | 2016089702 | A1 | 6/2016 |
| WO | 2016141082 | A1 | 9/2016 |
| WO | 2016161254 | A1 | 10/2016 |
| WO | 2016181384 | A2 | 11/2016 |
| WO | 2017004278 | A1 | 1/2017 |
| WO | 2017089289 | A1 | 6/2017 |
| WO | 2017091624 | A1 | 6/2017 |
| WO | 2017105600 | A1 | 6/2017 |
| WO | 2017184988 | A1 | 10/2017 |
| WO | 2017187177 | A1 | 11/2017 |
| WO | 2017205816 | A1 | 11/2017 |
| WO | 2018009614 | A1 | 1/2018 |
| WO | 2018067748 | A1 | 4/2018 |
| WO | 2018120104 | A1 | 7/2018 |
| WO | 2018136799 | A1 | 7/2018 |
| WO | 2018204568 | A1 | 11/2018 |
| WO | 2019043702 | A1 | 3/2019 |
| WO | 2019077482 | A1 | 4/2019 |
| WO | 2019094440 | A1 | 5/2019 |
| WO | 2019213493 | A1 | 11/2019 |
| WO | 2019246381 | A1 | 12/2019 |
| WO | 2020081393 | A1 | 4/2020 |
| WO | 2020124058 | A1 | 6/2020 |
| WO | 2021011738 | A1 | 1/2021 |

OTHER PUBLICATIONS

Unger, Jeff, et al., "Glucose Control in the Hospitalized Patient," Emerg. Med 36(9):12-18 (2004).

"Glucommander FAQ" downloaded from https://adaendo.com/GlucommanderFAQ.html on Mar. 16, 2009.

Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.

Letters to the Editor regarding "Glucose Control in Critically Ill Patients," N Engl J Med 361: 1, Jul. 2, 2009.

"Medtronic is Leading a Highly Attractive Growth Market," Jun. 2, 2009.

Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.

Davidson, Paul C., et al. "Pumpmaster and Glucommander," presented at the MiniMed Symposium, Atlanta GA, Dec. 13, 2003.

Kanji S., et al. "Reliability of point-of-care testing for glucose measurement in critically ill adults," Critical Care Med, vol. 33, No. 12, pp. 2778-2785, 2005.

Krinsley James S., "Severe hypoglycemia in critically ill patients: Risk factors and outcomes," Critical Care Med, vol. 35, No. 10, pp. 1-6, 2007.

International Search Report and Written Opinion for the International Patent Application No. PCT/US2021/016283, mailed Jun. 2, 2021, 15 pages.

Farkas et al. "Single-Versus Triple-Lumen Central Catheter-Related Sepsis: A Prospective Randomized Study in a Critically Ill Population" The American Journal of Medicine, Sep. 1992, vol. 93, p. 277-282.

Davidson, Paul C., et al., A computer-directed intravenous insulin system shown to be safe, simple,and effective in 120,618 h of operation, Diabetes Care, vol. 28, No. 10, Oct. 2005, pp. 2418-2423.

R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.

Gorke, A "Microbial Contamination Of Haemodialysis Catheter Connections" Journal of Renal Care, European Dialysis & Transplant Nurses Association.

Lovich et al. "Central venous catheter infusions: A laboratory model shows large differences in drug delivery dynamics related to catheter dead volume" Critical Care Med 2007 vol. 35, No. 12.

Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.

Schlegel et al, "Multilumen Central Venous Catheters Increase Risk for Catheter-Related Bloodstream Infection: Prospective Surveillance Study" Infection 2008; 36: 322-327.

Wilson, George S., et al., Progress toward the Development of an Implantable Sensor for Glucose, Clin. Chem., vol. 38, No. 9, 1992, pp. 1613-1617.

Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.

International Search Report and Written Opinion, International Application No. PCT/US2010/033794 mailed Jul. 16, 2010 (OPTIS.247VPC).

International Search Report and Written Opinion in PCT/US2008/079641 (Optis.203VPC) dated Feb. 25, 2009.

Berger, "Measurement of Analytes in Human Serum and Whole Blood Samples by Near-Infrared Raman Spectroscopy," Ph.D. Thesis, Massachusetts Institute of Technology, Chapter 4, pp. 50-73, 1998.

Berger, "An Enhanced Algorithm for Linear Multivariate Calibration," Analytical Chemistry, vol. 70, No. 3, pp. 623-627, Feb. 1, 1998.

Billman et. al.,"Clinical Performance of an In line Ex-Vivo Point of Care Monitor: A Multicenter Study," Clinical Chemistry 48: 11, pp. 2030-2043, 2002.

Widness et al., "Clinical Performance on an In-Line Point-of-Care Monitor in Neonates"; Pediatrics, vol. 106, No. 3, pp. 497-504, Sep. 2000.

Finkielman et al., "Agreement Between Bedside Blood and Plasma Glucose Measurement in the ICU Setting"; retrieved from http://www.chestjournal.org; CHEST/127/5/May 2005.

Glucon Critical Care Blood Glucose Monitor, Glucon; retrieved on Dec. 29, 2010 from http://www.glucon.com.

Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.

Vonach et al., "Application of Mid-Infrared Transmission Spectrometry to the Direct Determination of Glucose in Whole Blood," Applied Spectroscopy, vol. 52, No. 6, 1998, pp. 820-822.

Muniyappa et al., "Current Approaches for assessing insulin sensitivity and resistance in vivo: advantages, imitations, and appropriate usage," AJP-Endocrinol Metab, vol. 294, E15-E26, first published Oct. 23, 2007.

International Preliminary Report on Patentability for the International Patent Application No. PCT/US2019/053603, mailed Apr. 8, 2021, 9 pages.

(56) References Cited

OTHER PUBLICATIONS

International Search Report and Written Opinion for the International Patent Application No. PCT/US2019/053603, mailed Jan. 7, 2020, 16 pages.
Dassau et al., "Detection of a meal using continuous glucose monitoring: Implications for an artificial [beta]-cell." Diabetes Care, American Diabetes Association, Alexandria, VA, US, 31(2):295-300 (2008).
Cameron et al., "Probabilistic Evolving Meal Detection and Estimation of Meal Total Glucose Appearance Author Affiliations", J Diabetes Sci and Tech,Vol., Diabetes Technology Society ;(5):1022-1030 (2009).
Lee et al., "A closed-loop artificial pancreas based on model predictive control: Human-friendly identification and automatic meal disturbance rejection", Biomedical Signal Processing and Control, Elsevier, Amsterdam, NL, 4(4):1746-8094 (2009).
Anonymous: "Fuzzy control system", Wikipedia, Jan. 10, 2020. URL: https://en.wikipedia.org/w/index.php?title=Fuzzy_control_system&oldid=935091190.
An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.
International Search Report and Written Opinion for the InternationalPatent Application No. PCT/US2021/017441, mailed May 25, 2021, 12 pages.
Mirko Messori et al: "Individualized model predictive control for the artificial pancreas: In silico evaluation of closed-loop glucose control", IEEE Control Systems, vol. 38, No. 1, Feb. 1, 2018, pp. 86-104.
International Search Report and Written Opinion for the International Patent Application No. PCT/US2021/017662, mailed May 26, 2021, 14 pages.
Anonymous: "Reservoir Best Practice and Top Tips" Feb. 7, 2016, URL: https://www.medtronic-diabetes.co.uk/blog/reservoir-best-practice-and-top-tips, p. 1.
Gildon Bradford: "InPen Smart Insulin Pen System: Product Review and User Experience" Diabetes Spectrum, vol. 31, No. 4, Nov. 15, 2018, pp. 354-358.
International Search Report and Written Opinion for the International Patent Application No. PCT/US2021/016050, mailed May 27, 2021, 16 pages.
International Search Report and Written Opinion for the International Patent Application No. PCT/US2020/065226, mailed May 31, 2021, 18 pages.
International Search Report and Written Opinion for the International Patent Application No. PCT/US2021/017659, mailed May 31, 2021, 13 pages.
Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.
Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.
Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.
Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.
E. Atlas et al., "MD-Logic Artificial Pancreas System: A pilot study in adults with type 1 diabetes", Diabetes Care, vol. 33, No. 5, Feb. 11, 2010, pp. 1071-1076.
European Search Report for the European Patent Application No. EP03743667, dated Jul. 22, 2008.
International Search Report and Written Opinion mailed Sep. 9, 2016, issued in PCT Patent Application No. PCT/US2016/037189, 12 pages.
Preliminary Report on Patentability mailed Dec. 21, 2017, issued in PCT Patent Application No. PCT/US2016/037189.
U.K. Intellectual Property Office, GB Application No. GB 1401587.9, "Search Report under Section 17(5)" Aug. 11, 2015, 1 page.
International Search Report and Written Opinion for PCT Application No. PCT/GB2015/050247, May 8, 2015, 14 pages.
Extended Search Report mailed Nov. 24, 2017, issued in European Patent Application No. 15779465.2, 10 pages.
International Search Report and Written Opinion for PCT Application No. PCT/US15/26875, mailed Jan. 18, 2016, 10 pages.
U.K. Intellectual Property Office, GB Application No. GB 1401588.7, "Search Report under Section 17(5)" Aug. 17, 2015, 1 page.
U.K. Intellectual Property Office, GB Application No. GB 1401589.5, "Search Report under Section 17" Jul. 27, 2015, 1 page.
International Search Report and Written Opinion for PCT Application No. PCT/GB2015/050250, May 7, 2015, 9 pages.
3GPP TS 23.003 V10.0.0.0 Numbering, addressing and identification. Dec. 2010.
International Search Report and Written Opinion for PCT Application No. PCT/GB2015/050251, Jun. 12, 2015, 9 pages.
European Search Report for the European Patent Application No. EP19194241, dated Oct. 22, 2019, 6 pages.
International Preliminary Report on Patentability for PCT/US2017/061095, issued on May 14, 2019, 6 pages.
International Search Report and Written Opinion for PCT/US18/52468, mailed on Feb. 26, 2019, 16 pages.
International Search Report and Written Opinion for PCT/US2017/061095, mailed on Feb. 20, 2018, 8 pages.
Andrenko et al., "EM Analysis of PBG Substrate Microstrip Circuits for Integrated Transmitter Front End" MMET Proceedings, 295-297 (2000).
Bardi et al., "Plane Wave Scattering From Frequency-Selective Surfaces by the Finite-Element Method" IEEE Transactions on Magnetics 38(2):641-644 (2002).
Chappell et al., "Composite Metamaterial Systems for Two-Dimensional Periodic Structures" IEEE, 3840387 (2002).
Cheng et al., "Preparation and Characterization of (Ba, Sr) TiO3 thin films using interdigitial electrodes" Microelectronic Engineering, 66:872-879 (2003).
Clavijo et al., "Design Methodology for Sievenpiper High-Impedance Surfaces: An Artificial Magnetic Conductor for Positive Gain Electrically Small Antennas" IEEE Transactions on Antennas and Propagation, 51(10):2678-2690 (2003).
Diaz et al., "Magnetic Loading of Antificial Magnetic Conductors for Bandwidth Enhancement" IEEE, 431-434 (2003).
Hansen "Effect of a High-Impedance Screen on a Dipole Antenna" IEEE Antennas and Wireless Propagation Letter, 1:46-49 (2002).
Joshi et al., "Processing and Characterization of Pure and Doped Ba0.6Sr0.4TiO3 thin films for tunable microsave applications" Mat. Res. Soc. Symp. Proc., 656E:DD4.9.1-DD4.9.6 (2001).
Kern et al., "Active Negative Impedance Loaded EBG Structures for the Realization of Ultra-Wideband Artificial Magnetic Conductors" IEEE, 427-430 (2003).
Kern et al., "The Synthesis of Metamaterial Ferrities for RF Applications Using Electromagnetic Bandgap Structures" IEEE, 497-500 (2003).
Kern et al., "Ultra-thin Electromagnetic Bandgap Absorbers Synthesized via Genetic Algorithms" IEEE, 1119-1122 (2003).
Kuhn et al., "Characterization of novel mono- and bifacially active semi-transparent crystalline silicon solar cells" IEEE Transactions on Electron Devices, 46(10): 2013-2017 (1999).
Kretly et al., "The Influence of the Height Variation on the Frequency Bandgap in an AMC, Artificial magnetic Conductor for Wireless Applications: an EM Experimental Design Approach" Proceedings SBMO/IEEE MTT-S IMOC, 219-223 (2003).
Lee et al., "Investigation of Electromagnetic Bandgap (EBG) Structures for Antenna Pattern Control" IEEE, 1115-1118 (2003).
Mckinzie III et al., "Mitigation of Multipath Through the Use of an Artificial Magnetic Conductor for Precision CPS Surveying Antennas" IEEE, 640-643; Date of Conference: Jun. 16-21, 2002.

(56) References Cited

OTHER PUBLICATIONS

Monorciho et al., "Synthesis of Artificial Magnetic Conductors by Using Multilatered Frequency Selective Surfaces" IEEE Antennas and Wireless Propagation Letters, 1:196-1999 (2002).

Mosallaei et al. "Periodic Bandgap and Effective Dielectric Materials in Electromagnetics: Characterization and Applications in Nanocavities and Waveguides" IEEE Transcations on Antennas and Propagation, 51(3):549-563 (2003).

Pontes et al., "Study of the dielectric and ferroelectric properties of chemically processed BaxSr1-xTiO3 thin films" Thin Solid Films, 386(2)91-98 (2001).

Rogers et al., "AMCs Comprised of Interdigital Capacitor FSS Layers Enable Lower Cost Applications" IEEE, 411-414 (2003).

Sievenpiper et al., "Two-Dimensional Beam Steering Using an Electrically Tunable Impedance Surface" IEEE Transactions on Antennas and Propagation, 51(10):2713-2722(2003).

Sun et al., "Efficiency of Various Photonic Bandgap (PBG) Structures" 3rd Int'l. Conf. on Microwave and Millimeter Wave Technology Proceedings, 1055-1058 (2002).

Tsunemine et al., "Pt/BaxSr(1-x)TiO3/Pt Capacitor Technology for 0.15 micron Embedded Dynamic Random Access Memory" Jap. J. Appl. Phys., 43(5A):2457-2461 (2004).

Vest "Metallo-organic decomposition (MOD) processing of ferroelectric and electro-optic films: A review" Ferroelectrics, 102(1):53-68 (1990).

Viviani et al., "Positive Temperature Coefficient of Electrical Resistivity below 150k of Barium Strontium Titanate" J. Amer. Ceram. Soc. 87(4): 756-758 (2004).

Weily et al., "Antennas Based on 2-D and 3-D Electromagnetic Bandgap Materials" IEEE, 847-850 (2003).

Yang et al., "Surface Waves of Printed Antennas on Planar Artificial Periodic Dielectric Structures" IEEE Transactions on Antennas and Propagation 49(3): 444-450 (2001).

Zhang et al., "Planar Artificial magnetic Conductors and Patch Antennas" IEEE Transactions on Antennas and Propagation, 51(10):2704-2712 (2003).

Ziroff et al., "A Novel Approach for LTCC Packaging Using a PBG Structure for Shielding and Package Mode Suppression" 33rd European Microwave Conference-Munich 419-422 (2003).

International Search Report and Written Opinion for Application No. PCT/US17/61336, mailed on Jan. 25, 2018, 9 pages.

"Graph Chart." iconfinder.com. Aug. 15, 2016. Accessed Apr. 21, 2020. Available online at URL: https://www.iconfinder.com/iconsets/graph-chart-2>.

"Circular Progress Indicator Component for React." reactscript.com. Dec. 2, 2016. Accessed Sep. 9, 2020. Available online at URL: <http://reactscripts.com/circular-progress-indicator-component-react/>.

Kruska, Michal. "Circle progress bar." dribbble.com. Oct. 18, 2012. Accessed Apr. 21, 2020. Available online at URL: <https://dribbble.com/shots/775718-Circle-progress-bar>.

"C# custom control <circle progress bar) Xamarian Forms." stackoverflow.com. May 22, 2016. Accessed Apr. 21, 2020. Available online at URL: <https://stackoverflow.com/questions/37379868/c-sharp-custom-control-circle-progress-bar-xamarin-forms>.

International Search Report and Written Opinion for Application No. PCT/US2021/047685 mailed on Dec. 6, 2021, 15 pages.

International Search Report and Written Opinion for the International Patent Application No. PCT/US2021/055745, mailed Feb. 14, 2022, 13 pages.

"Circular Loader." dribbble.com. Nov. 19, 2015. Accessed Jul. 24, 2019. Available online at URL: https://dribbble.com/shots/2362441-Circular-Loader (Year: 2015).

"Creating NSSlider with 2 knobs (range slider)." stackoverflow.com. May 6, 2015. Accessed Oct. 25, 2018. Available online at URL: <https://stackoverflow.com/questions/30082809/creating-nsslider-with-2- - knobs-range-slider> (Year: 2015).

"How to do a Round Slider." freecodecamp.org. Comment from Aug. 2018. Accessed Jul. 24, 2019. Available online at URL: https://www.freecodecamp.org/forum/t/how-to-do-a-round-slider/220375 (Year: 2018).

"Tick and cross circle shape icon . . . " depositphotos.com. Aug. 27, 2016. Accessed Feb. 1, 2019. Available online at URL:<https://depositphotos.com/121291612/stock-illustration-tick-and-cross-circle-shape.html> (Year: 2016).

"Vector-Vector Illustration of Preloader / Buffer Shapes, or Dials with Knobs." 123rf.com. Date not available. Accessed Oct. 25, 2018. Available online at URL: <https://www.123rf.com/photo_37292689_stock-vector-vector-illustration- -of-preloader-buffer-shapes-or-dials-with-knobs.html> (Year: N/A).

Gad, Tess. "Framer Cheat Sheet: Slider & Range Sliders." blog.framer.com. Jun. 12, 2017. Accessed Oct. 25, 2018. Available online at URL: <https://blog.framer.com/framer-cheat-sheets-slider-range-sliders-3dd2e5a4621d> (Year: 2017).

Obaizamomwan, Osas. "How to use the new features in iOS 9 Notes App." iphonehacks.com. Sep. 12, 2015. Accessed Apr. 24, 2018. Available online at URL: https://www.iphonehacks.com/2015/09/how-to-use-the-new-features-in-ios-9-notes-app.html.

International Search Report and Written Opinion for the International Patent Application No. PCT/US21/064056, mailed Apr. 4, 2022, 12 pages.

International Search Report and Written Opinion for the International Patent Application No. PCT/US21/064170, mailed Apr. 20, 2022, 12 pages.

Anonymous: "AndroidAPS ComponentOverview", AndroidAPS documentation, Nov. 12, 2020 (Nov. 12, 2020), pp. 1-7, Retrieved from the Internet: URL:https://github.com/openaps/AndroidAPSdocs/blob/199ef86a900adf4b3d9c32f605eb11047bd3d62f/docs/EN/Module/module.rst [retrieved on Apr. 11, 2022] the whole document.

Team Section—Qonto, by Christophe Kerebel, dated Dec. 12, 2018, dribbble.com [online]. Retrieved Jul. 1, 2022 from Internet <URL: https://dribbble.com/shots/5676730-Team-Section-Qonto> (Year: 2018).

International Search Report and Written Opinion for the International Patent Application No. PCT/US2020/052125, mailed Aug. 12, 2020, 15 pages.

International Search Report and Written Opinion for the International Patent Application No. PCT/US2020/050332, mailed Sep. 12, 2020, 12 pages.

European Patent Office, "Notification of Transmittal of the ISR and the Written Opinion of the International Searching Authority, or the Declaration," in PCT Application No. PCT/GB2015/050248, Jun. 23, 2015, 12 pages.

International Search Report and Written Opinion for the International Patent Application No. PCT/US2021/012246, mailed Apr. 13, 2021, 15 pages.

International Search Report and Written Opinion for the International Patent Application No. PCT/US2021/013639, mailed Apr. 28, 2021, 14 pages.

International Search Report and Written Opinion for the International Patent Application No. PCT/US2020/063326, mailed May 3, 2021, 17 pages.

European Search Report for the European Patent Application No. 21168591, mailed Oct. 13, 2021, 4 pages.

International Search Report and Written Opinion for the International Patent Application No. PCT/US2021/041954, mailed Oct. 25, 2021, 13 pages.

International Search Report and Written Opinion for the International Patent Application No. PCT/US2021/022694, mailed Jun. 25, 2021, 13 pages.

International Search Report and Written Opinion for the International Patent Application No. PCT/US2021/017664, mailed May 26, 2021, 16 pages.

International Search Report and Written Opinion for the International Patent Application No. PCT/US2022/012896, mailed Apr. 22, 2022, 15 pages.

International Search Report and Written Opinion for the International Patent Application No. PCT/US2022/013470, mailed May 6, 2022, 14 pages.

(56) References Cited

OTHER PUBLICATIONS

International Search Report and Written Opinion for the International Patent Application No. PCT/US2022/013473, mailed May 6, 2022, 13 pages.
International Search Report and Written Opinion for the International Patent Application No. PCT/US2022/019079, mailed Jun. 2, 2022, 14 pages.
International Search Report and Written Opinion for the International Patent Application No. PCT/US2022/018453, mailed Jun. 2, 2022, 13 pages.
International Search Report and Written Opinion for the International Patent Application No. PCT/US22/018700, mailed Jun. 7, 2022, 13 pages.
International Search Report and Written Opinion for the International Patent Application No. PCT/US22/019080, mailed Jun. 7, 2022, 14 pages.
International Search Report and Written Opinion for the International Patent Application No. PCT/US22/019664, mailed Jun. 7, 2022, 14 pages.
International Search Report and Written Opinion for International Patent Application No. PCT/US2021/051027, mailed on Jan. 7, 2022, 16 pages.
International Search Report and Written Opinion for International Patent Application No. PCT/US2021/052372, mailed Jan. 26, 2022, 15 pages.
International Search Report and Written Opinion for the International Patent Application No. PCT/US2021/046607, mailed Jan. 31, 2022, 20 pages.
International Search Report and Written Opinion for the International Patent Application No. PCT/US21/060618, mailed Mar. 21, 2022, 15 pages.
Herrero Pau et al: "Enhancing automatic closed-loop glucose control in type 1 diabetes with an adaptive meal polus calculator -in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.
Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.
Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].
Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/ master/lib/determine-basal/determine-basal.js [retrieved on Jun. 6, 2022] line 116-line 118, line 439-line 446.
Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].
Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/Issues/2473 [retrieved on Jun. 6, 2022].
International Search Report and Written Opinion for the International Patent Application No. PCT/US2021/052855, mailed Dec. 22, 2021, 11 pages.
International Search Report and Written Opinion for the International Patent Application No. PCT/US2021/047771, mailed Dec. 22, 2021, 11 pages.
Medication Bar Code System Implementation Planning Section I: A Bar Code Primer for Leaders, Aug. 2013.
Medication Bar Code System Implementation Planning Section II: Building the Case for Automated Identification of Medications, Aug. 2013.
Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.
Fox, Ian G.; Machine Learning for Physiological Time Series: Representing and Controlling Blood Glucose for Diabetes Management; University of Michigan. ProQuest Dissertations Publishing, 2020. 28240142. (Year: 2020).
International Search Report and Written Opinion for the International Patent Application No. PCT/US2023/019254, mailed Jul. 25, 2023, 14 pages.
International Search Report and Written Opinion for the International Patent Application No. PCT/US2023/019256, mailed Jul. 10, 2023, 12 pages.
Maahs David M. et al: "A Randomized Trial of a Home System to Reduce Nocturnal Hypoglycemia in Type 1 Diabetes", Diabetes Care, vol. 37, No. 7, Jun. 12, 2014 (Jun. 12, 2014), pp. 1885-1891, Retrieved from the Internet: URL:https://diabetesjournals.org/care/article-pdf/37/7/1885/486685/1885.pdf>.
International Search Report and Written Opinion for the International Patent Application No. PCT/US2021/047690, mailed Jan. 14, 2022, 13 pages.
International Search Report and Written Opinion for the International Patent Application No. PCT/US2022/055745, mailed Feb. 14, 2022, 13 pages.
International Search Report and Written Opinion for the International Patent Application No. PCT/US2021/053162, mailed Mar. 28, 2022, 18 pages.
International Search Report and Written Opinion for the International Patent Application No. PCT/US2021/064041, mailed Apr. 29, 2022, 11 pages.
International Search Report and Written Opinion for the International Patent Application No. PCT/US2022/015809, mailed Jun. 20, 2022, 15 pages.
International Search Report and Written Opinion for International Patent Application No. PCT/US2022/029012, mailed Aug. 19, 2022, 12 pages.
Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".
Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).
Dassau et al., "Real-Time Hypoglycemia Prediction Suite Using Contineous Glucose Monitoring," Diabetes Care, vol. 33, No. 6, 1249-1254 (2010).
International Search Report and Written Opinion for International Patent Application No. PCT/US17/53262, mailed on Dec. 13, 2017, 8 pages.
Van Heusden et al., "Control-Relevant Models for Glucose Control using A Priori Patient Characteristics", IEEE Transactions on Biomedical Engineering, vol. 59, No. 7, (Jul. 1, 2012) pp. 1839-1849.
Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).
Bequette, B.W., and Desemone, J., "Intelligent Dosing Systems": Need for Design and Analysis Based on Control Theory, Diabetes Technology and Therapeutics 9(6): 868-873 (2004).
Parker et al., "A Model-Based Algorithm for Blood Gucose Control in Type 1 Diabetic Patients." IEEE Transactions on Biomedical Engineering, 46 (2) 148-147 (1999).
International Search Report and Written Opinion for International Patent Application No. PCT/US2017/015601, mailed May 16, 2017, 12 pages.

(56) References Cited

OTHER PUBLICATIONS

International Search Report and Written Opinion for the International Patent Application No. PCT/US2018/018901, mailed on Aug. 6, 2018, 12 pages.
International Search Report and Written Opinion for International Patent Application No. PCT/US2018/052467, mailed Jan. 4, 2019, 13 pages.
"How to Create a QR Code that Deep Links to Your Mobile App", Pure Oxygen Labs, web<https://pureoxygenlabs.com/how-to-create-a-qr-codes-that-deep-link-to-your-mobile-app/>. Year:2017.
"Read NFC Tags with an iPHone App on iOS 11", GoToTags, Sep. 11, 2017, web <https://gototags.com/blog/read-nfc-tags-with-an-iphone-app-on-ios-11/> (Year:2017).
International Search Report and Written Opinion for International Patent Application No. PCT/US2016/063350, mailed on Mar. 27, 2017, 9 pages.
Extended Search Report mailed Aug. 13, 2018, issued in European Patent Application No. 16753053.4, 9 pages.
International Search Report and Written Opinion for International Patent Application No. PCT/US16/18452, mailed on Apr. 29, 2015, 9 pages.
International Preliminary Report on Patentability mailed Aug. 31, 2017, issued in PCT Patent Application No. PCT/US2016/018452, 7 pages.
International Search Report and Written Opinion for International Patent Application No. PCT/US2019/055862, mailed on Mar. 11, 2020.
International Search Report and Written Opinion for Application No. PCT/US2019/030562, Sep. 25, 2019, 19 pages.
Lee, et al. "The Clinical Case for the Integration of a Ketone Sensor as Part of a Closed Loop Insulin Pump System," Journal of Diabetes Science and Technology 2019, vol. 13(5) 967-973 (Year: 2019).
Laffel, et al., "ISPAD Clinical Practice Consensus Guidelines 2018: Sick day management in children and adolescents with diabetes," (Year: 2018).
Mencher, et al., "Sick Day Management," First Online: Feb. 13, 2021, pp. 125-133. (Year: 2021).
Fuchs, et al. "Benefits and Challenges of Current Closed-Loop Technologies in Children and Young People With Type 1 Diabetes," Mini Review published: Apr. 30, 2021 (Year: 2021).
Lee, Melissa H. et al: "The Clinical Case for the Integration of a Ketone Sensor as Part of a Closed Loop Insulin Pup System", Journal of Diabetes Science and Technology Diabetes Technology Society, vol. 13(5), Dec. 31, 2019 (Dec. 31, 2019), pp. 967-973.
Rometo, David et al: "Perioperative Glycemic Management of Patients Undergoing Bariatric Surgery", Current Diabetes Reports, Current Science, Philadelphia, VA, US, vol. 16, No. 4, Feb. 15, 2016 (Feb. 15, 2016), pp. 1-8.

* cited by examiner

Sehar & Iftar Time April / May 2022

Fiqh Jafria: Suhoor Time -10min | Iftar Time + 10min

| | Day | Sehar | Dhuhr | Asr | Iftar | Isha |
|---|---|---|---|---|---|---|
| 1 | 02, Sat | **04:14 AM** | 11:53 AM | 03:24 PM | **06:08 PM** | 07:38 PM |
| 2 | 03, Sun | **04:14 AM** | 11:53 AM | 03:24 PM | **06:08 PM** | 07:38 PM |
| 3 | 04, Mon | **04:12 AM** | 11:52 AM | 03:24 PM | **06:09 PM** | 07:39 PM |
| 4 | 05, Tue | **04:10 AM** | 11:52 AM | 03:24 PM | **06:10 PM** | 07:40 PM |
| 5 | 06, Wed | **04:09 AM** | 11:52 AM | 03:24 PM | **06:10 PM** | 07:40 PM |
| 6 | 07, Thu | **04:08 AM** | 11:51 AM | 03:24 PM | **06:11 PM** | 07:41 PM |
| 7 | 08, Fri | **04:07 AM** | 11:51 AM | 03:24 PM | **06:12 PM** | 07:42 PM |

FIG. 3

MEDICAMENT ADAPTATION AND SAFETY MONITORING

RELATED APPLICATIONS

This application claims the benefit of U.S. Provisional Patent Application No. 63/333,149, filed Apr. 21, 2022, the entire contents of which are incorporated herein by reference in their entirety.

BACKGROUND

Assessment of the performance of a medication delivery algorithm, such as automated drug delivery (ADD) algorithms, are often executed in a stepwise process, where a significant amount of drug delivery data and glucose measurement data is processed. Changes in the ADD algorithm that can result in improved glucose control outcome.

Fasting over predictive patterns changes insulin requirements. The specific challenges in diabetic patients when fasting is used as part of a dieting technique may potentially induce changes in glucose metabolism and drug sensitivity because the fasting may entail distinctive changes in food and fluids consumption. Similarly, the undertaking of fasting during a religious event, such as Ramadan, Lent, Passover, or a similar event may impact blood glucose measurement data over a lengthy period of time (e.g., 1 month). Diabetes patients who fast are predisposed to excessive glycogenolysis, gluconeogenesis and increased ketogenesis. Risks for hypoglycemia, hyperglycemia, diabetic ketoacidosis, and dehydration are elevated.

It would be beneficial if there were processes and systems to adapt medication delivery during fasting periods and non-fasting periods as well as processes and systems to monitor a user's safety as they undertake periods of fasting.

BRIEF SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

Disclosed is a controller of a drug delivery system. The controller includes a processor, a user interface, a memory, and a communication circuitry. The processor is operable to execute programming instructions. The user interface includes a display and user input circuitry. The memory is operable to store the programming instructions. The communication circuitry is coupled to the processor operable to receive and transmit wireless communication signals. The processor is operable to receive, via the user interface, an indication of a fasting event or a period of fasting for a user; and modify a drug delivery schedule based on the fasting event or the period of fasting, where such modifications can occur before, during, and/or after the period of fasting or fasting event.

In a further exemplary aspect, a drug delivery system is provided. The drug delivery system includes a processor, a user interface, a memory, and a communication circuitry. The processor is operable to execute programming instructions. The user interface includes a display and user input circuitry. The memory is operable to store the programming instructions. The communication circuitry is coupled to the processor operable to receive and transmit wireless communication signals. The processor is operable to receive, via the user interface, an indication of a period of fasting for a user; and modify a drug delivery schedule based on the period of fasting.

BRIEF DESCRIPTION OF THE DRAWINGS

FIG. 3 illustrates an example of a portion of a calendar suitable for use by a fasting application in the examples disclosed herein.

DETAILED DESCRIPTION

The following discussion provides a framework of an ADD algorithm to adjust to when a user partakes in fasting for a period of time, which may last for a period of hours or for multiple days.

A type of medication delivery algorithm (MDA) may include an "artificial pancreas" algorithm-based system, or more generally, an artificial pancreas (AP) application. For ease of discussion, the computer programs and computer applications that implement the medication delivery algorithms or applications may be referred to herein as an "AP application," an "ADD algorithm," or an "MDA." An AP application may be configured to provide automated delivery of medicament based on an analyte sensor(s) input, such as signals received from an analyte sensor(s), such as a continuous glucose monitor, ketone sensor or the like. The signals from the analyte sensor(s) may contain glucose measurement values, ketone measurement values, timestamps, or the like.

In addition, or alternatively, while the disclosed examples may have been described with reference to a closed loop algorithmic implementation, variations of the disclosed examples may be implemented to enable open loop or hybrid closed loop use. These implementations allow for use of different modalities of delivery of insulin such as smart pen, syringe or the like. For example, the disclosed AP application and algorithms may be operable to perform various functions related to open loop operations, such as the generation of prompts requesting the input of information such as diabetes type, weight, or age. Similarly, a requested dosage amount of medicament, such as insulin, may be received by the AP application or algorithm from a user via a user interface. Other open-loop actions may also be implemented by adjusting user settings or the like in an AP application or algorithm.

Systems, devices, computer readable media and methods in accordance with the present disclosure are now described more fully hereinafter with reference to the accompanying drawings, where one or more examples are shown. The systems, devices, and methods described herein may be embodied in many different forms and are not to be construed as being limited to the examples set forth herein. Instead, these examples are provided so the disclosure is thorough and complete, and may fully convey the scope of the techniques and devices to those skilled in the art. Each of the systems, devices, media, and methods disclosed herein provides one or more advantages over conventional systems, components, and methods.

Figure 1:
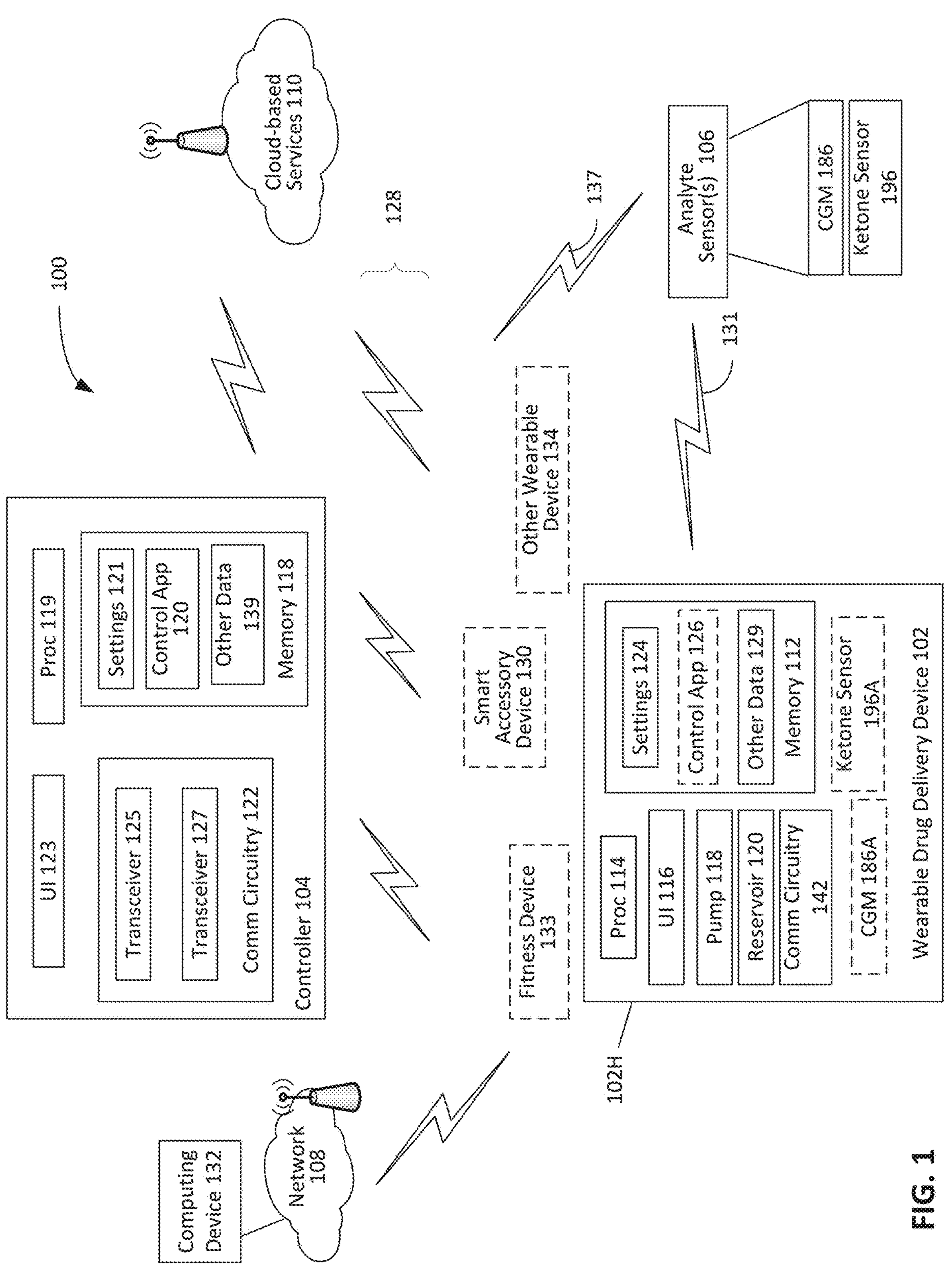
FIG. 1 illustrates an example of a system that is suitable to implement the subject matter described herein.

FIG. 1 illustrates an exemplary drug delivery system operable to implement the examples disclosed herein.

In some examples, the drug delivery system 100 is suitable for delivering a liquid medicament, such as insulin to a user in accordance with the disclosed embodiments. The drug delivery system 100 may include a wearable drug delivery device 102, a controller 104 and an analyte sensor (s) 106.

The wearable drug delivery device 102 may be a wearable device that is worn on the body of the user. The wearable drug delivery device 102 may be directly coupled to a user (e.g., directly attached to a body part and/or skin of the user via an adhesive, or the like). In an example, a surface of the wearable drug delivery device 102 may include an adhesive to facilitate attachment to the skin of a user.

The wearable drug delivery device 102 may include a processor 114. The processor 114 may be implemented in hardware, software, or any combination thereof. The processor 114 may, for example, be a microprocessor, a logic circuit, a field programmable gate array (FPGA), an application specific integrated circuit (ASIC) or a microprocessor coupled to a memory. The processor 114 may maintain a date and time as well as be operable to perform other functions (e.g., calculations or the like). The processor 114 may be operable to execute a control application 126 stored in the memory 112 that enables the processor 114 to direct operation of the wearable drug delivery device 102. The control application 126 may control insulin delivery to the user per an ADD control approach as describe herein. For example, the control application 126 may be an ADD algorithm. The memory 112 may hold settings 124 for a user, such as ADD algorithm settings, such as maximum insulin delivery, insulin sensitivity settings, total daily insulin (TDI) settings and the like. The memory may also store other data 129, such as ketone values, total daily insulin values, glucose measurement values from analyte sensor(s) 106 or controller 104, insulin dosage amounts (both basal and bolus) and the like from previous minutes, hours, days, weeks, or months. The analyte sensor(s) 106 may be operable to collect physiological condition data, such as ketone values, ketone values with a time stamp, glucose measurement values (also referred to herein as "blood glucose values" or "blood glucose"), glucose measurement values and a timestamp, both ketone values and glucose values that may be shared with the wearable drug delivery device 102, the controller 104 or both. In an additional example, the analyte sensor(s) 106 may include multiple sensors, such as a continuous glucose monitor 186 and a ketone sensor(s) 196. In a further example, the wearable drug delivery device 102 may optionally include a continuous glucose monitor 186A and a ketone sensor 196A, which may be removably incorporated or fully integrated within the wearable drug delivery device 102. For example, the continuous glucose monitor 186A and the ketone sensor 196A may be incorporated in one or more housings 102H of the wearable drug delivery device 102. Note that ketones may also be detected using a breath sensor (which is not shown but may be incorporated in the controller 104) or urine content sensor and stored in the respective memories 118 and 112 via a user input of the ketone levels; however, a subcutaneous ketone sensor(s) gives more accurate information and is more continuous. As described herein, the MDA and ADD system is described based on receiving ketone values received subcutaneously. Use of a ketone breath sensor or urine sensor as part of or in addition to the analyte sensor(s) 106 may delay receipt of the ketone values and modifications to the system 100 may be made.

For example, the communication circuitry 142 of the wearable drug delivery device 102 may be operable to communicate with the analyte sensor(s) 106 and the controller 104 as well as the devices 130, 133 and 134. The communication circuitry 142 may be operable to communicate via Bluetooth, cellular communication, near field communication (NFC) and/or other wireless protocols. While not shown, the memory 112 may include both primary memory and secondary memory. The memory 112 may include random access memory (RAM), read only memory (ROM), optical storage, magnetic storage, removable storage media, solid state storage or the like.

The wearable drug delivery device 102 may include a reservoir 120. The reservoir 120 may be operable to store liquid drugs, medicaments, or therapeutic agents suitable for automated delivery, such as, insulin, glucagon-like peptide-1 (GLP-1) receptor agonist, pramlintide, glucose-dependent insulinotropic polypeptide (GIP), other hormones, or co-formulations of two or more of glucagon, GLP-1, pramlintide, and insulin; as well as pain relief drugs, such as opioids or narcotics (e.g., morphine, or the like), methadone, blood pressure medicines, chemotherapy drugs, fertility drugs, or the like.

A fluid path to the user may be provided via tubing and a needle/cannula (not shown). The fluid path may, for example, include tubing coupling the wearable drug delivery device 102 to the user (e.g., via tubing coupling a needle or cannula to the reservoir 120). The wearable drug delivery device 102 may be operable based on control signals from the processor 114 to expel the liquid drugs, medicaments, or therapeutic agents, such as insulin, from the reservoir 120 to deliver doses of the drugs, medicaments, or therapeutic agents, such as the insulin, to the user via the fluid path. The processor 114 may be operable to cause insulin to be expelled from the reservoir 120.

There may be one or more communications links 128 with one or more devices physically separated from the wearable drug delivery device 102 including, for example, a controller 104 of the user and/or a caregiver of the user and/or a sensor(s) 106. The communication links 128 may include any wired or wireless communication link operating according to any known communications protocol or standard, such as Bluetooth®, NFC, Wi-Fi, a near-field communication standard, a cellular standard, or any other wireless protocol. The analyte sensor(s) 106 may communicate with the wearable drug delivery device 102 via a wireless communication link 131 and/or may communicate with the controller 104 via a wireless communication link 137.

The wearable drug delivery device 102 may also include a user interface 116, such as an integrated display device for displaying information to the user, and in some embodiments, receiving information from the user. For example, the user interface 116 may include a touchscreen and/or one or more input devices, such as buttons, knob(s), or a keyboard that enable a user to provide an input.

In addition, the processor 114 may be operable to receive data or information from the analyte sensor(s) 106 as well as other devices that may be operable to communicate with the wearable drug delivery device 102.

The wearable drug delivery device 102 may interface with a network 108. The network 108 may include a local area network (LAN), a wide area network (WAN) or a combination therein. A computing device 132 may be interfaced with the network, and the computing device may communicate with the insulin delivery device 102. The computing device 132 may be a healthcare provider device through which a user's controller 104 may interact to obtain information, store settings and the like. The ADD algorithm operating, as or in cooperation with, the control application 120 may present a graphical user interface on the computing device 132 enabling the input and presentation of information related to the ADD algorithm and the example techniques and processes described herein.

The drug delivery system 100 may include an analyte sensor(s) 106 for sensing the levels of one or more analytes of a user. The analyte levels may be used as physiological condition data and be sent to the controller 104 and/or the wearable drug delivery device 102. The sensor(s) 106 may be coupled to the user by, for example, adhesive or the like and may provide information or data on one or more medical conditions and/or physical attributes of the user. The sensor (s) 106 may be a continuous glucose monitor (CGM), ketone sensor, or another type of device or sensor(s) that provides glucose measurements and/or ketone measurements. The sensor(s) 106 may be physically separate from the wearable drug delivery device 102 or may be an integrated component thereof. The sensor(s) 106 may provide the processor 114 and/or processor 119 with physiological condition data indicative of measured or detected glucose levels of the user. The information or data provided by the sensor(s) 106 may be used to modify a medicament delivery schedule and thereby cause the adjustment of drug delivery operations of the wearable drug delivery device 102.

The drug delivery system 100 may also include the controller 104. In the depicted example, the controller 104 may include a processor 119 and a memory 118. The controller 104 may be a special purpose device, such as a dedicated personal diabetes manager (PDM) device. The controller 104 may be a programmed general-purpose device that is a portable electronic device, such as any portable electronic device, smartphone, smartwatch, fitness device, tablet or the like including, for example, a dedicated processor, such as processor, a micro-processor or the like. The controller 104 may be used to program or adjust operation of the wearable drug delivery device 102 and/or the sensor(s) 106. The processor 119 may execute processes to control the delivery of the medicament, drug, or therapeutic agent to the user for the purpose of managing a user's blood glucose and/or ketone levels. The processor 119 may also be operable to execute programming code stored in the memory 118. For example, the memory 118 may be operable to store a control application 120, such as an ADD algorithm for execution by the processor 119. The control application 120 may be responsible for controlling the wearable drug delivery device 102, including the automated delivery of medicament, a drug, or therapeutic agent based on recommendations and instructions from the ADD algorithm, such as those recommendations and instructions described herein.

The memory 118 may store one or more applications, such as control application 120, and settings 121 for the drug delivery device 102 like those described above. In addition, the memory 118 may be operable to store other data 139 and/or computer programs, such as drug delivery history, glucose measurement values over a period of time, total daily insulin values, ketone values, and the like. For example, the memory 118 is coupled to the processor 119 and operable to store programming instructions, such as the control application 120 and settings 121, and data, such as other data 139, related to a glucose of a user and/or data related to an amount of insulin expelled by the wearable drug delivery device 102.

The controller 104 may include a user interface (UI) 123 for communicating with the user. The user interface 123 may include a display, such as a touchscreen, for displaying information. The touchscreen may also be used to receive input when it is a touch screen. The user interface 123 may also include input elements, such as a keyboard, button, knob or the like. In an operational example, the user interface 123 may include a touchscreen display (including a display and user input circuitry, such as touch sensitive circuits and the like) controllable by the processor 119 and be operable to present a graphical user interface and receive inputs via the user input circuitry, the touchscreen display may be operable to generate a signal indicative of the respective diet types, number of days, diet cycles, keto days, sick day mode, sickness symptoms, intermittent fasting mode, fasting mode, religious fasting mode, location information, calendar information, or the like. The touchscreen display, under control of the processor 119, may be operable to, in response to the received input, generate a response to a user's drug treatment regimen as well as cause the presentation of prompts on a graphical user interface as described with reference to the later examples described with reference to FIGS. 2-10. The graphical user interfaces discussed herein with respect to the later examples may be generated by the processor 119 of the controller 104 and be presented on the UI 123.

The controller 104 may interface via a wireless communication link of the wireless communication links 128 with a network, such as a LAN or WAN or combination of such networks that provides one or more servers or cloud-based services 110 via communication circuitry 122. The communication circuitry 122, which may include transceivers 127 and 125, may be coupled to the processor 119. The communication circuitry 122 may be operable to transmit communication signals (e.g., command and control signals) to and receive communication signals (e.g., via transceivers 127 or 125) from the wearable drug delivery device 102 and the analyte sensor(s) 106. In an example, the communication circuitry 122 may include a first transceiver, such as 125, that may be a Bluetooth transceiver, which is operable to communicate with the communication circuitry 122 of the wearable drug delivery device 102, and a second transceiver, such as 127, that may be a cellular or Wi-Fi transceiver operable to communicate via the network 108 with computing device 132 or with cloud-based services 110.

The cloud-based services 110 may be operable to receive and store user history information, such as glucose measurement values over a set period of time (e.g., days, months, years), a drug delivery history that includes insulin delivery amounts (both basal and bolus dosages) and insulin delivery times, types of insulin delivered, indicated meal times, glucose measurement value trends or excursions or other user-related diabetes treatment information, specific factor settings including default settings, present settings and past settings, or the like.

Other devices, like smart accessory device 130 (e.g., a smartwatch or the like), fitness device 133 and other wearable device 134 may be part of the drug delivery system 100. These devices may communicate with the wearable drug delivery device 102 to receive information and/or issue commands to the wearable drug delivery device 102. These devices 130, 133 and 134 may execute computer programming instructions to perform some of the control functions otherwise performed by processor 114 or processor 119. These devices 130, 133 and 134 may include user interfaces, such as touchscreen displays for displaying information such as current glucose level, medicament on board such as insulin on board, drug delivery history, or other parameters or treatment-related information and/or receiving inputs, such as those described with reference to the examples of FIGS. 1-10. The display may, for example, be operable to present a graphical user interface for providing input, such as request a change in basal insulin dosage or delivery of a bolus of insulin. These devices 130, 133 and 134 may also have wireless communication connections with the sensor(s) 106 to directly receive glucose level data or receive in parallel a presentation of the graphical user interface as shown in FIG. 1.

In another operational example, the controller 104 may be operable to execute programming code that causes the processor 119 of the controller 104 to perform the following functions. The processor 119 of the controller 104 may execute an ADD algorithm that is one of the control applications 120 stored in the memory 118. The processor may be operable to present graphical user interfaces as described herein on a user interface that is at least one component of the user interface 123. The user interface 123 may be a touchscreen display controlled by the processor 119, and the user interface 123 is operable to present a graphical user interface that offers an input of a subjective insulin need parameter usable by the ADD algorithm. The processor 119 may cause presentation on a user interface of a user device, a graphical user interface offering an input device that enables input of a subjective medicament need parameter (e.g., subjective to the user, or based on the user's desire). The ADD algorithm may generate instructions for the pump 118 to deliver basal medicament to the user or the like.

The processor 119 is also operable to collect physiological condition data related to the user from sensors, such as the analyte sensor(s) 106 or heart rate data, for example, from the fitness device 133 or the smart accessory device 130. In an example, the processor 119 executing the ADD algorithm may determine a dosage of medicament to be delivered based on the collected physiological condition of the user and/or a specific factor determined based on the subjective medicament need parameter. The processor 119 may output a control signal via one of the transceivers 125 or 127 to the wearable drug delivery device 102. The outputted signal may cause the processor 114 to deliver command signals to the pump 118 to deliver an amount of the determined dosage of medicament in the reservoir 120 to the user based on an output of the ADD algorithm. The processor 119 may also be operable to perform calculations to update or establish settings of the ADD algorithm as discussed as herein. Modifications to the ADD algorithm settings may be stored in the memory 118, for example, as settings 121.

A wearable drug delivery device 102, typically, has a lifecycle that is based on the amount of liquid drug that is stored in a reservoir 120 of the wearable drug delivery device 102 and/or the amount of the liquid drug delivered to the user. An ADD application or algorithm may use a number of parameters, such as glucose measurement values, total daily medicament, medicament onboard, and the like, when making the determination of an amount of the liquid drug to have delivered. In an operational example, the processor 119 of the controller 104 may be operable to receive evaluate the effectiveness of the ADD algorithm's control of the drug delivery device 102. For example, the processor 119 may be operable to utilize historical data accessible by the processor in an evaluation of past performance of the ADD algorithm and generate recommendations for adjusting settings of the ADD algorithm accordingly as described in more detail with reference to the examples in the figures.

While the system 100 is described with reference to delivery of insulin and the use of an ADD algorithm, the system 100 may be operable to implement a drug delivery regimen via a medication delivery algorithm using a number of different liquid or therapeutic drugs/medicaments. A liquid drug may be or include any drug in liquid form capable of being administered by a drug delivery device via a subcutaneous cannula, including, for example, insulin, glucagon-like peptide-1 (GLP-1), glucose-dependent insulinotropic polypeptide (GIP), pramlintide, glucagon, co-formulations of two or more of GLP-1, GIP, pramlintide, and insulin; as well as pain relief drugs, such as opioids or narcotics (e.g., morphine, or the like), methadone, blood pressure medicines, chemotherapy drugs, fertility drugs, or the like.

Insulin Delivery Adaptation for Predictive Fasting Patterns

Type 1 diabetics may be adversely affected by periods of fasting. The following discussion addresses the specific challenges in diabetic patients undertaking fasting as a diet or wellness technique (e.g., intermittent fasting, time restricted eating (e.g., eating only during 6-8 hours per day), 5:2 diet (5 days one diet/2 days different diet), warrior diet, Keto diet, or the like) as well as during a holiday, such as Ramadan, Passover, or Lent. In more detail, wellness technique fasting entails distinctive changes in food and/or fluids consumption that could potentially induce changes in glucose metabolism and insulin sensitivity. Diabetic patients who fast are predisposed to excessive glycogenolysis (e.g., production of glucose from glycogen), gluconeogenesis (e.g., production of glucose from non-carbohydrate sources) and increased ketogenesis (e.g., production of ketones from fatty acids and ketogenic amino acids). Additionally, risks for hypoglycemia, hyperglycemia, diabetic ketoacidosis, and dehydration are also elevated. The following discussion provides techniques implemented through a computer application that interacts with the MDA of the ADD system.

Figure 2:
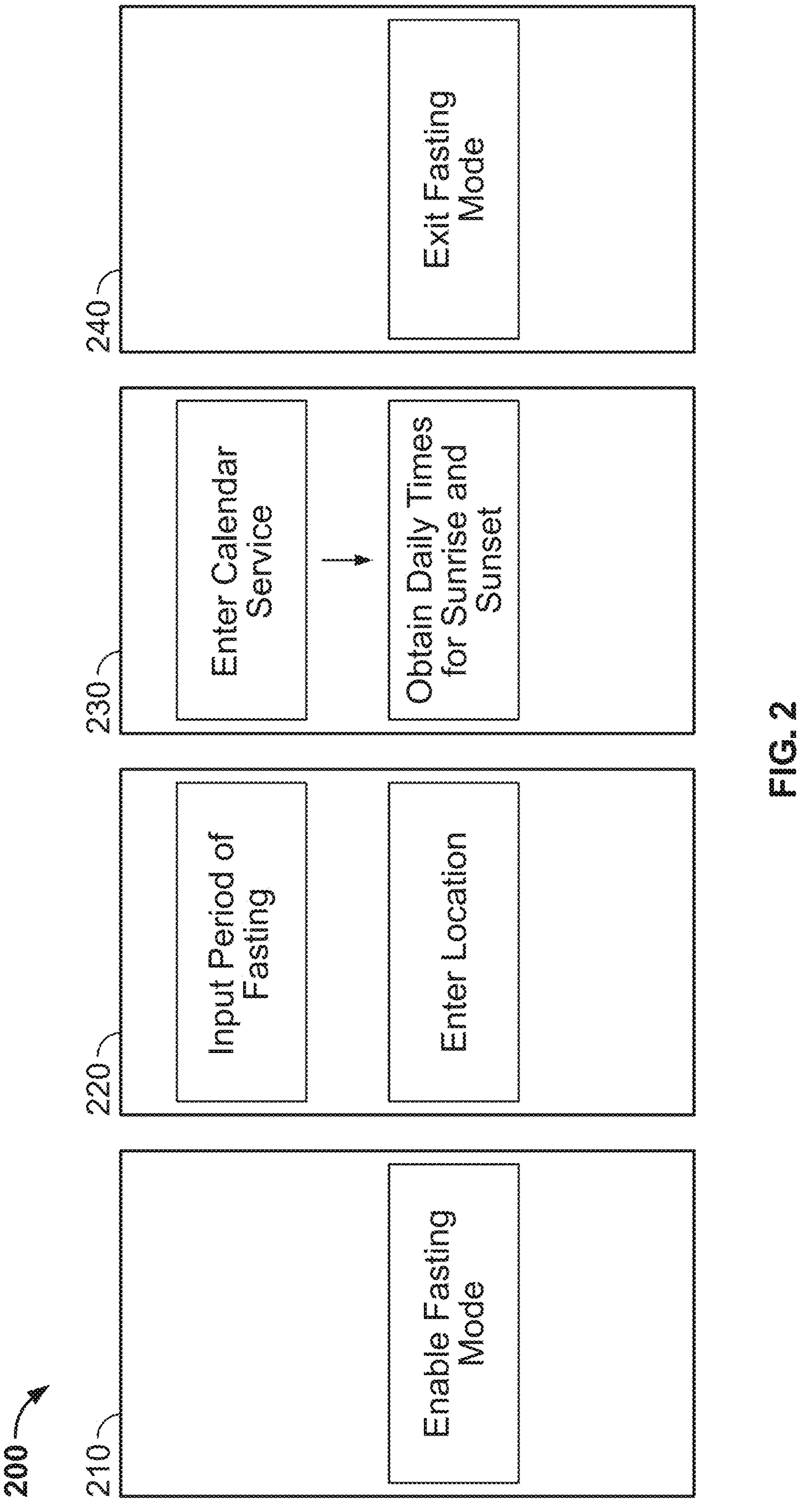
FIG. 2 illustrates another block diagram of the graphical user interface suitable for use to indicate fasting.

FIG. 2 illustrates a block diagram of the graphical user interface suitable for use to indicate fasting or to initiate a fasting mode, such as during a religious holiday.

The graphical user interface 200 is operable to present one or more different windows to collect information related to the user's fasting. For example, window 210 may be a prompt presented to the user that enables the user to initiate a fast or fasting mode. In response to the input at window 210, the computer application may begin modifying a drug delivery schedule based on the indication of fasting. For example, after the fast mode has been enabled, the computer application may generate a prompt, such as "Input Period of Fasting," "Fasting Event," or "Enter location," or a prompt to enter the type of fast, or a combination of the foregoing, which is presented in another window, such as 220. The period of fasting may be several hours, such as 8 PM-12 PM, Sunset to Sunrise, Sunrise to Sunset, 6 AM-4 PM, or the like. The location of the user may be useful to determine time zones, the times for Sunrise and Sunset at the user's location, and the like.

Alternatively, or additionally, the computer application, at 230, may generate a further prompt that produces a request to enter a calendar service, such as Google® calendar, Yahoo® calendar or Outlook® calendar. The calendar service may also be coupled to a service (e.g., a cloud based or internet based service) that indicates the times for Sunrise and Sunset on a daily basis. Alternatively, the system may store in memory different fasting periods that correspond to different fasting events, such as religious holidays or dieting regimens. The system may receive a time and date from other applications running on the system (e.g., a clock and calendar on a smartphone) and if the user selects to initiate a fasting mode, the system may ask the user via a GUI whether the fasting mode corresponds to a particular event (e.g., a fasting event) based on the current date and time or an upcoming date and time.

At 240, the computer application may, for example, at the end of the period of fasting or on occasion (e.g., every 24 hours or every couple of days or after each indicated fasting period), generate a prompt inquiring if the user would like to "Exit Fasting Mode."

A more detailed discussion of GUI window 230 is made with reference to FIG. 3, which illustrates an example of a portion of a calendar suitable for use in a fasting application of the examples disclosed herein.

In the FIG. 3 example, the fasting application may be operable to receive an indication of a holiday that requires fasting, such as Ramadan or Lent. As shown in FIG. 3, a calendar 300 of the dawn (Sehar) and dusk (Iftar) times for the portion of the year and location (based on Doha, Kuwait) can be extracted from a calendar. Of course, other calendars and locations may be used to determine dawn or dusk as well as other times, such as work start or work end times, or the like. For example, fasting during Ramadan lasts 29 to 30 days each year, and the glycemic outcomes of diabetic patients on ADD systems can be significantly improved during this time of prolonged fasting if the system is aware that the user is fasting. In the case of Ramadan, the times for dawn (Sehar) and dusk (Iftar) are those times shown in the week during April and May of the calendar 300. The Sehar or dawn is when fasting starts and Iftar or dusk is when fasting ends. Typically, adherents to Ramadan eat a meal approximately prior to dawn and do not eat another meal until approximately dusk. As a result of the fasting, basal medicament needs are typically lower in the day (reduced by 20% up to 40% from baseline). Hyperglycemia is a challenge after the evening meal (Iftar) and the predawn meal (Sehar). Of course, the described examples may be used at other times as well.

In fasting situations, glycemic outcomes may be improved by the MDA of the ADD system by addressing and/or providing a GUI for fasting, a daytime medicament adaptivity algorithm, a dusk-to-dawn adaptivity algorithm, auxiliary sensors and/or safety monitoring and alerts. While the following examples of FIGS. 4-6 refer to dawn and dusk and to an approximately 12 hour fasting period, the fasting period may vary and the described intervals may be altered proportionately. In other fasting examples, "dawn" may be analogous to time for a pre-fasting period meal and "dusk" may be analogous to a post-fasting period meal, or the like. The system may receive a time, such as a current time and/or a dawn and dusk time, from other applications running on the system (e.g., a weather and/or clock and calendar app running on a smartphone) and may adjust medicament delivery settings accordingly if the particular user fast is influenced by time of day or calendar day. Thus, after initiating a "fasting mode," the user may be prompted to indicate whether the fast corresponds to an X, Y, or Z event based on the current time and/or day. If the user confirms that the fast corresponds to X event, and X event corresponds to fasting during particular periods of the day and/or particular days, the system will know that the user intends to fast during those particular periods of day and/or days and can adjust medicament delivery, accordingly, as explained further below.

Referring back to FIG. 2, in an operational example of the GUI 200 for fasting, the GUI 200 allows the user to set a fasting mode. For example, a user can invoke the Fast Mode (at window 210) as show in the GUI 200 through the portable diabetes manager (PDM) or controller, such as 106 of FIG. 1. The user may enable fast mode (210). The user may also set their location (220) via the GUI; alternatively, the user's location may be determined based on the location of the device or controller 104, e.g., from a geolocation service or app running on the device or controller 104. In an example, the location may be used to interface with a calendar service (at 230) running on the device or controller 104 or retrieved from a cloud-based service 110 that has the dawn (Sehar) and dusk times (Iftar) for the location which may be used to automatically determine a mealtime after dusk and a dawn mealtime for each day. Exemplary times are shown in FIG. 3. At the conclusion of a fasting period, the user may exit Fast Mode (240) at which time the processor may return the medicament delivery settings to baseline. In an example, if a number of fasting days (e.g., 28 to 30 days or a recurring 1 day or another period of time) have elapsed and the user has not requested an exit from Fast Mode, the Fast Mode may be automatically exited by the PDM or controller. The fast exit mode may also be used by the user in case there is a particular reason to exit the fast early. The user may restart again if the user wishes by pressing "Enable Fasting Mode" or a similar type of soft button, again (e.g., as presented in window 210 of FIG. 2).

Day Time Medicament Adaptivity

When fasting (including intermittent fasting) occurs for an extended period of time, such as 2-3 days or longer, a user's daily medicament requirements may change. Since fasting during Ramadan, for example, is for an extended period of time, a user's medicament requirements are likely altered at least during that period of time. The manner in which the computer application and MDA respond may be configured to respond is described with reference to FIGS. 4A-6. For example, during the day, the 3 hours after start of a dawn or a sunrise meal (Sehar) and 3 hours prior to the start of a dusk meal (Iftar), may be referred to as fasting period modification points. The nominal or baseline medicament need will only correspond to fasting basal medicament needs that are typical for the user when fasting. However, during prolonged fasting periods (e.g., 14 hours or longer) the medicament needs may be further reduced several hours into the fasting period. As such, the MDA when modifying a drug delivery schedule based on the period of fasting may make multiple modifications to the drug delivery schedule. As used herein, "the drug delivery schedule" may include an amount of drug to be delivered over particular time periods during a treatment period (e.g., 12, 16, 24 or 48 hours or other periods). For example, the fasting basal medicament dosage (e.g., a baseline dosage) may be 2 Units (U) per hour during the time period.

Figures 4A, 4B:
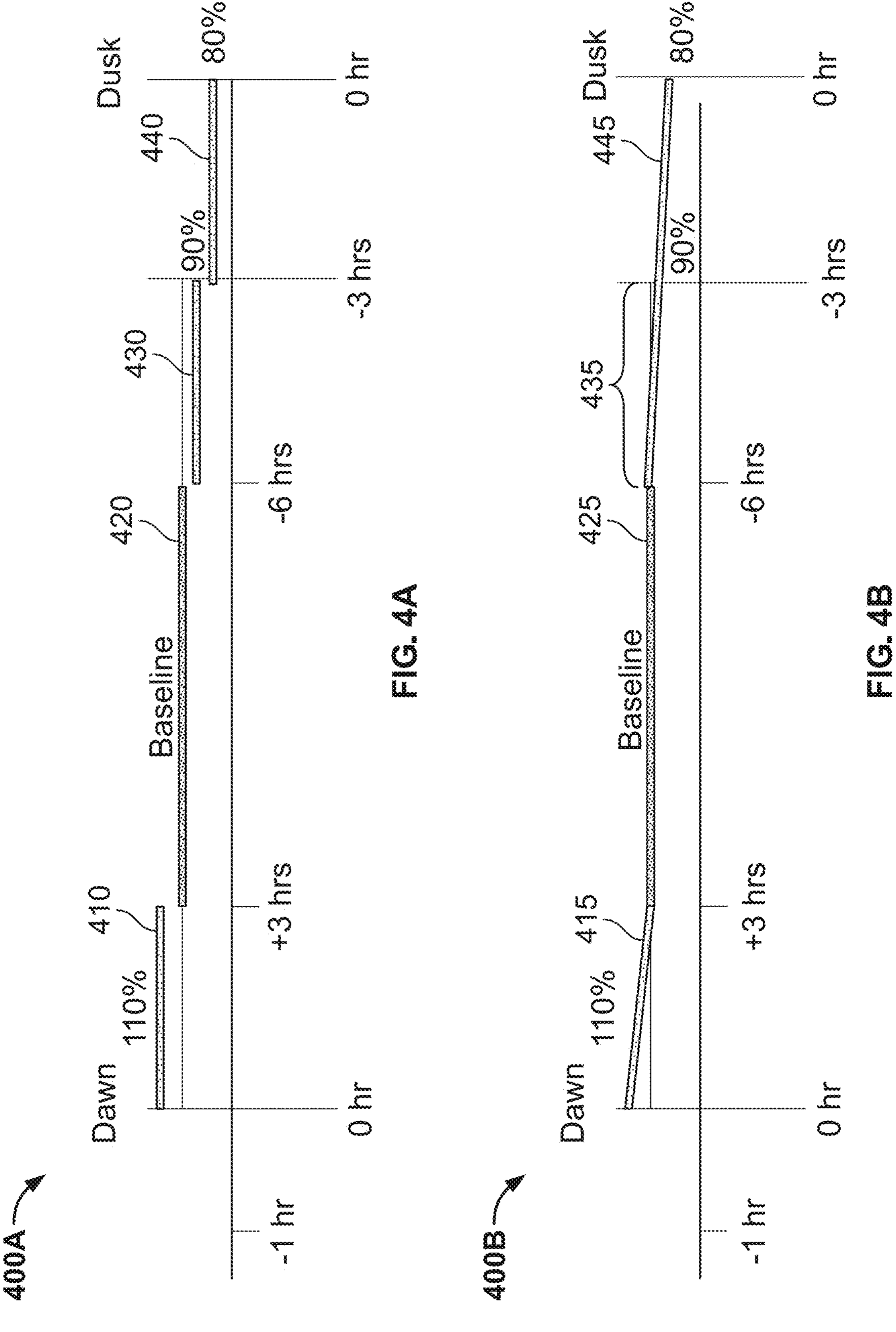
FIG. 4A illustrates an example of a dawn-to-dusk basal modulation delivery schedule according to the disclosed subject matter.
FIG. 4B illustrates an alternative example of a dawn-to-dusk basal delivery schedule modulated according to the disclosed subject matter.

The processor may adjust basal medicament delivery according to a drug delivery schedule for basal delivery of medicament as illustrated in FIG. 4A and outlined in Table 1 below.

TABLE 1

| Basal Delivery Dawn to Dusk | | | |
|---|---|---|---|
| Dawn to Dawn + 3 hrs. | Dawn + 3 hrs. to dawn + 6 hrs. | Dawn + 6 hrs. to Dusk − 3 hrs. | Dusk − 3 hrs. to Dusk |
| Baseline*110% | Baseline | Baseline*90% | 80%*Baseline |

The example drug delivery schedule as shown in basal delivery schedule 400A may begin increasing a basal rate for a first time threshold after receipt of the indication of the period of fasting. For example, the MDA may increase the basal rate by approximately 10% above a baseline insulin (shown as 110%) delivery rate (e.g., 8 U/hour), at 410, for 3 hours after dawn (0 dawn hour to +3 hrs (where +3 indicates the number of hours since the start of the fasting period)) to act as a supplement to the bolus for the dawn meal taken at approximately 0 hour. The delivery of the bolus dosage is not shown in this example, but is described in another section herein. For the next 3 hours of the fasting period (e.g., from +3 hrs until −6 hours (where −6 indicates the number of remaining hours in the fasting period)), the basal medicament delivery rate is set to the baseline medicament delivery rate of the user (420). In the example, at 420, the MDA maintains the basal rate at a baseline value between a first time threshold after receipt of the indication of the period of fasting and a second time threshold after receipt of the indication of the period of fasting.

The processor executing the MDA, when modifying the drug delivery schedule based on the period of fasting, may be operable to reduce a basal delivery rate for a period of time prior to an end of the period of fasting. For example, after the baseline medicament delivery rate has been delivered for the 3 hours from +3 hrs to −6 hrs of the fasting period, the basal medicament delivery rate may be reduced by 10% (shown as 90%) from the baseline medicament delivery rate (430). The basal delivery schedule is further modified from the baseline medicament delivery rate after the 3 hours (or up to 3 hours before dusk (−3 hrs to 0 dusk hour)). The basal medicament delivery rate is decreased, at 440, by 20% (shown as 80%) from the baseline basal medicament delivery rate (i.e., 100%) for 3 hours prior to dusk to start of dusk (i.e., −3 hrs to 0 dusk hour). The reductions in basal delivery rate may function as a safeguard against hypoglycemia. While the increases and decreases of basal delivery rate are described in percentage increments of 10%, these increments may have been other percentage increments, such as 12%, 8%, 20% or the like. Additionally, or alternatively, the percentage increments may have varied across time thresholds, where a time threshold may be a time start point such as 0 hours (hr), or a time duration, such as 3 hours or 0 hr to +3 hrs. For example, a first percentage increase may be a first percentage increment, such as 10% at a first time threshold, a second percentage increment, such as 5% at a second time threshold, and a third percentage increment, such as 15% at a third time threshold.

FIG. 4B illustrates an alternative example of a dawn-to-dusk basal modulation delivery schedule according to the examples discussed with reference to FIGS. 2 and 3. In the alternative example of FIG. 4B, the processor, when modifying the drug delivery schedule based on the period of fasting, may be operable to adjust a basal delivery rate according to a function that decreases basal rate delivery from a set percentage (e.g., 10%) to a baseline basal delivery rate, and from the baseline basal delivery rate to the set percentage (i.e., 10%) or another set percentage (e.g., 5%, 12% or 20%) under the baseline basal delivery rate over a duration of the period of fasting.

The drug delivery schedule 400B has similar time markings as those presented in 400A of FIG. 4A so a discussion of the similar features is not repeated.

In the basal delivery schedule 400B of FIG. 4B, the basal rate at 0 dawn hour (0 hr) is initially increased approximately 10% above baseline basal medicament delivery rate for the user during 415. In contrast to 410 of FIG. 4A, the initial 10% increase in basal rate in 415 is allowed to decrease to baseline basal medicament delivery rate after 3 hours (i.e., form time 0 hr to +3 hours). In the drug delivery schedule of FIG. 4B, the initial basal rate setting at 110% of the baseline medicament delivery rate may linearly decrease over 3 hours to the baseline medicament delivery rate (i.e., 100%). At the end of the initial 3 hours after dawn (e.g., at +3 hrs), the MDA may deliver medicament at the baseline basal delivery rate of the user (425). The delivery of medicament at the baseline basal delivery rate of the user may last for another 3 hours until time mark minus (—) 6 hours. At the −6 hour mark, the MDA may linearly decrease the basal rate (at 435) from the baseline basal medicament delivery rate (i.e., 100%) to end at 90% of the baseline basal delivery rate when the time mark −3 hrs is reached. From the −3 hrs time mark, the MDA may permit the basal rate to continue to linearly decrease from the 90% of the baseline basal delivery rate to 80% of the baseline basal delivery rate over the following 3 hours until the dusk 0 hr is reached (445).

While a linear decrease is shown in the example FIG. 4B, the decrease may follow any sort of function, such as a stair-step, exponential, logarithmic, or the like, that is reasonable for the drug treatment of the user.

The medicament delivered by the ADD algorithm may start with these nominal delivery schedules shown in FIGS. 4A and 4B, which may be adapted to deliver additional or reduced medicament based on a prediction of the user's glucose level and the user's current medicament on board (e.g., insulin on board (JOB)). The medicament delivery may be adapted by examining excursions in the glucose level as indicated by glucose measurements.

In addition to modifying the user's drug delivery schedule during the day (i.e., dawn to dusk), the MDA is also operable to modify the user's drug delivery schedule from dusk to dawn as part of a dusk-to-dawn medicament adaptivity process. For example, the processor may be operable to modify the can occur before, during, and/or after the period of fasting or fasting event.

Figures 5A, 5B:
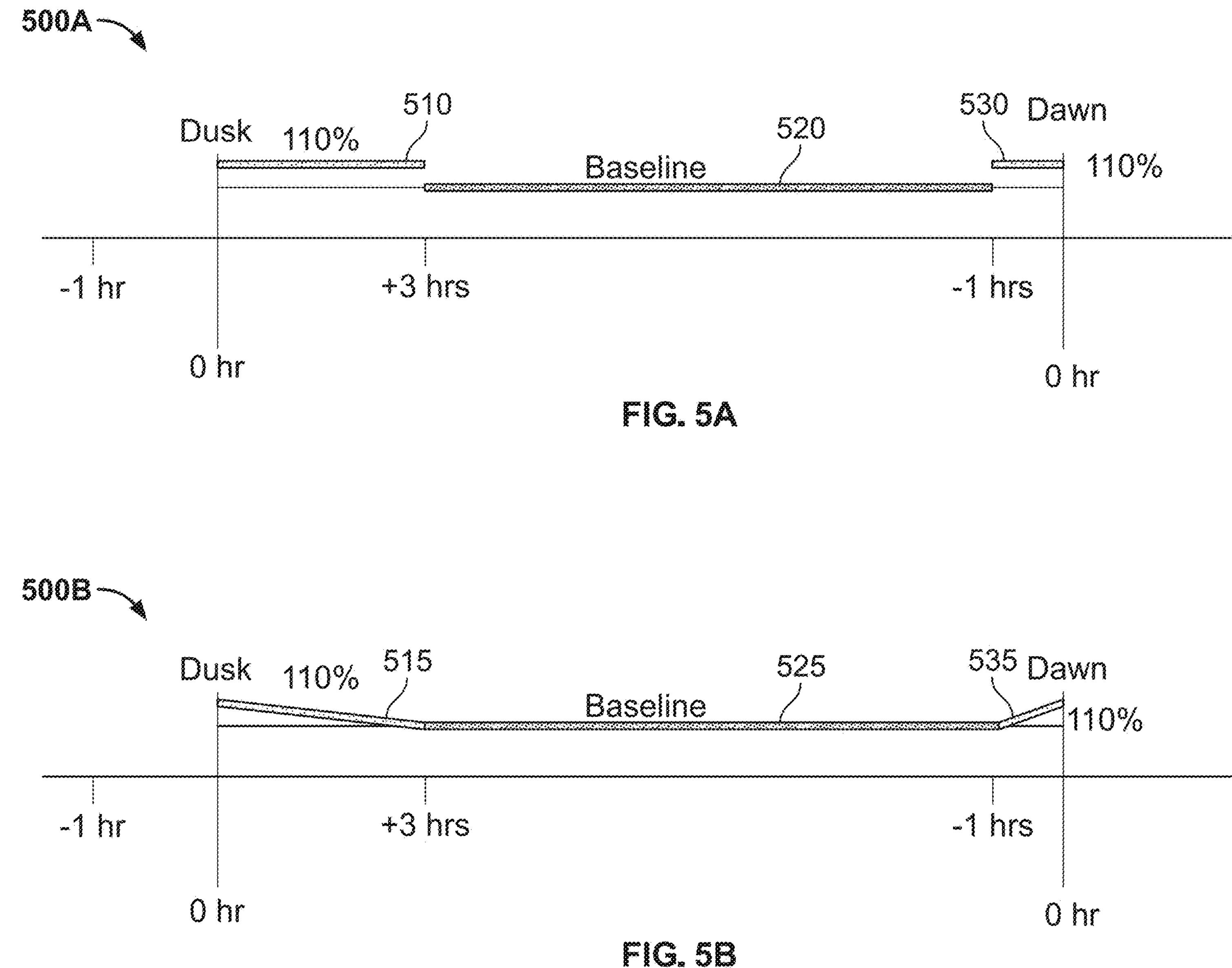
FIG. 5A illustrates an example of a dusk-to-dawn basal delivery schedule modulated according to the disclosed subject matter.
FIG. 5B illustrates an alternative example of a dusk-to-dawn basal delivery schedule modulated according to the disclosed subject matter.

FIG. 5A illustrates an example of a dusk-to-dawn modulated basal delivery schedule according to the disclosed subject matter.

The MDA executed by the processor may, at an end of the period of fasting, be operable to adjust a basal delivery rate up or down by a set percentage over a baseline basal rate for a first period of time, set the basal delivery rate to the baseline basal rate delivery for a second period of time, and/or increase or decrease the baseline basal delivery rate by a preset percentage over the baseline basal delivery rate for a third period of time.

As shown in more detail in the basal delivery schedule example of FIG. 5A, the processor when executing the MDA to implement the basal insulin delivery schedule 500A may keep the basal medicament delivery at approximately 110% of nominal basal for approximately 3 hours after the start of dusk (510). At the +3 hours' time mark, the basal delivery rate may be kept at the baseline basal delivery rate for the user, for example, from approximately +3 hours after dusk to approximately 1 hour prior to dawn (i.e., −1 hr. time mark) (520). At the −1 hr. time mark, the MDA may again increase the basal delivery rate 10% to 110% of the baseline basal delivery rate (530). The increased basal delivery rate of 110% of the basal delivery rate at 530 may continue until dawn (i.e., 0 hr. dawn).

FIG. 5B illustrates an alternative example of a dusk-to-dawn basal delivery schedule modulated according to the disclosed subject matter. In the examples, the period of fasting is dawn-to-dusk.

In the alternative basal delivery schedule 500B of FIG. 5B, the MDA as implemented by the processor may be operable, at the end of the period of fasting (i.e., dusk), to adjust basal delivery rate according to a function that decreases basal rate delivery from a preset percentage increase over a baseline basal delivery rate to the baseline basal delivery rate over a first period of time. The MDA may also set the basal delivery rate to the baseline basal rate delivery for a second period of time, and increase the baseline basal delivery rate to the preset percentage over the baseline basal delivery rate for a third period of time.

In an operational example, the MDA may gradually decrease (e.g., linearly in this example) the basal rate, for example, over the 3 hours after dusk from approximately 110% of the baseline basal delivery rate of the user. In the example, the MDA may cause the basal delivery rate at 0 hr dusk to be set initially at approximately 110% of the baseline basal delivery rate (515). In this and other examples, the baseline basal delivery rate may be a default value, may be input by the user, or preferably may be determined based on a total daily medicament delivered over a prior period (e.g., the total medicament delivered one day prior and divided by 2 (assuming a 50-50 split between basal and bolus medicament) and further divided by 24 (to determine an hourly basal baseline)). As time progresses, the basal delivery rate decreases (e.g., linearly) from the 110% of the baseline basal delivery rate to the baseline delivery rate at +3 hr. after dusk time mark (515). The decrease in the basal delivery rate may be a linear decrease. From the +3 hr. after dusk time mark until one hour prior to dawn (i.e., the −1 hrs. time mark), the basal delivery rate may remain at the basal baseline delivery rate of the user (525). At approximately 1 hour prior to dawn (i.e., the −1 hrs. time mark), the MDA may increase (e.g., linearly) the basal delivery rate from the baseline basal delivery rate to approximately 110% of the baseline basal delivery rate (535) as shown in basal medicament delivery schedule 500B.

While a linear decrease and a linear increase are shown in FIG. 5B, the decrease and increase may follow any sort of function, such as a stair-step, exponential, logarithmic, or the like, that is reasonable for the drug treatment of the user.

Since participants in the fast usually have a meal prior to the beginning of the period of fasting (e.g., dawn), and a daytime fast is typically broken at the end of the period of fasting (e.g., dusk), a bolus dosage of insulin may be given by the MDA for meal compensation at these times. The dosage of bolus insulin may be calculated as follows in Equation 1:

$$\text{Bolus Insulin} = x\%\ TDI + \frac{(\text{Blood Glucose} - \text{SetPoint})}{1800/TDI} - IOB$$

where the 1800 rule (i.e., 1800/TDI) is used for the correction factor, TDI is total daily insulin, the SetPoint variable is the user's target blood glucose level, variable x is any positive number (e.g., 5%, 8%, 10%, 12%, up to 20%, or the like), and IOB is the insulin on board (alternatively the 1600 rule (i.e., 1600/TDI) may be used in place of the 1800 rule). The correction factor and the IOB terms are expected to be small because of the already tapered basal insulin leading up to dusk.

Figure 6:
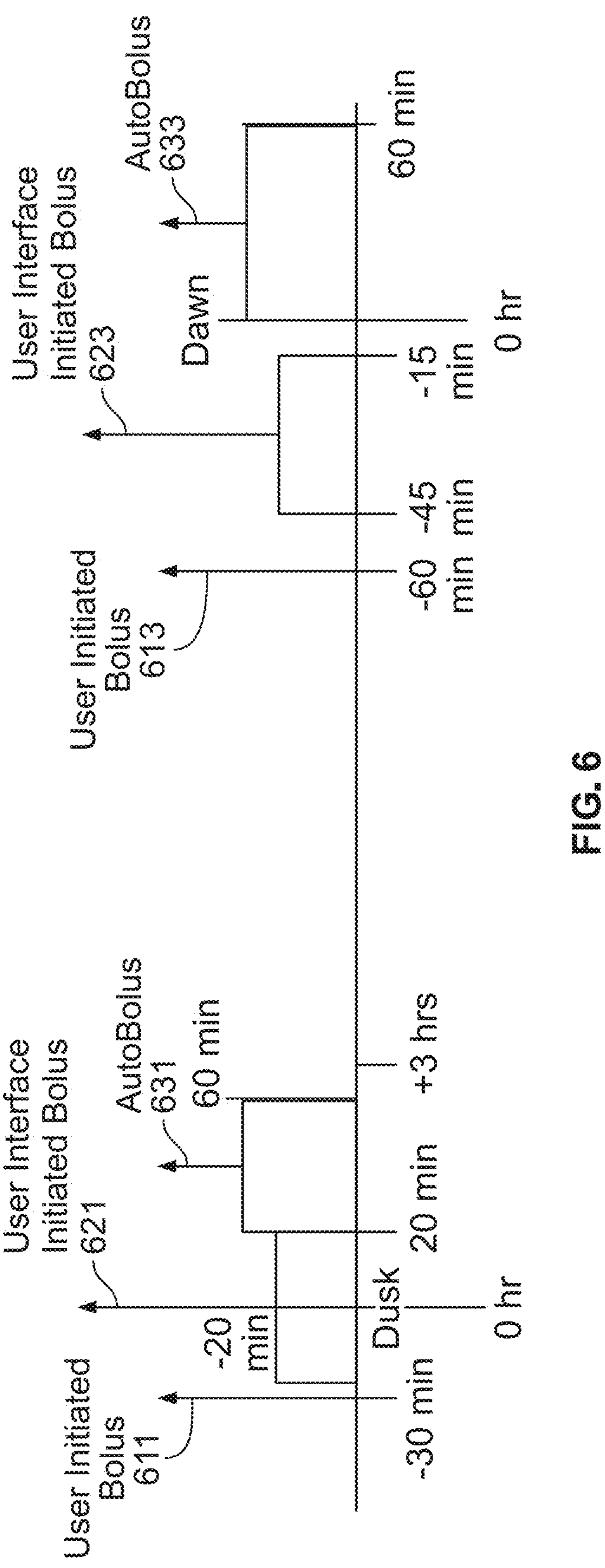
FIG. 6 illustrates an example of a bolus delivery schedule according to the examples discussed with reference to FIGS. 2 and 3.

FIG. 6 illustrates an example of a bolus delivery schedule in relation to the examples discussed with reference to FIGS. 4A, 4B, 5A and 5B. This bolus delivery schedule may operate automatically (or with user confirmation) when the system is in Fast Mode.

In an example, the bolus may be delivered to the user via three modalities, which are shown in FIG. 6 for ease of description and understanding. In the first modality (referred to as a user initiated bolus) 611 and 613, the bolus may be user initiated by the user signaling to the MDA that a meal has been consumed, is being consumed or is about to be consumed.

The second modality (referred to as a user interface initiated bolus), such as 621 and 623, can be a time bound initiation that may cause a bolus to be administered to a user automatically via a setting made in the user interface. For example, when the period of fasting is based on when dawn and dusk occur, the automated setting of when the bolus will be delivered may be determined via the calendar service that is called and set according to the times for dawn and dusk as shown in window 230 of FIG. 2. The second modality 621 and 623 may differ in the times they are implemented with respect to the end of the period of fasting and the beginning of the period of fasting, which are shown in this example, as dusk and dawn, respectively. For example, via the second modality 621, the approximate start of dusk and dawn may be based on a calendar service called and the obtained daily for sunrise and sunset. The bolus medicament may be administered automatically by the MDA, for example, within a window of time that is equally divided at the approximate start of dusk. The bolus medicament may be administered only after the user confirms the bolus delivery (e.g., after an automatic prompt by the system at the determined time (e.g., dusk or dawn)). Meanwhile, the second modality 623 may be scheduled to deliver a bolus that is also approximately near dawn, but accounts for a meal being consumed before the beginning of the period of fasting. As a result, the second modality 623 may be implemented in a manner different from second modality 621. The user interface initiated bolus 623 (or second modality 623) may be administered prior to the dawn, or beginning of the fasting period, for example, between 45 minutes prior to dawn (−45 min) and 15 minutes prior to dawn (−15 min).

When setting up the user interface initiated bolus 621 or 623, the processor may provide in the graphical user interface (similar to those shown in FIG. 2) suggested times for administering a bolus based on the times that the user indicates they will be starting the period of fasting and a time when they will be ending the period of fasting. Based on the user indicated starting and ending times the processor may set a window of time during which the user interface initiated bolus 621 is delivered and another window of time during which the user interface initiated bolus 623 is delivered. Alternatively, the processor may provide in the graphical user interface fields that allow the user to input a window of time that corresponds to delivery of the user interface initiated bolus 621 and the delivery of the user interface initiated bolus 623.

In the third modality 631 and 633, the bolus medicament may be administered as an AutoBolus function that is based on meal detection. Meal detection may be implemented by monitoring a user's glucose levels to detect changes in glucose levels that correspond or correlate with a user's consumption of a meal. A meal detection threshold may be a rate of change of the user's glucose (e.g., increases of 15%-25% or greater within 30 minutes, a change from 120 mg/dL to 180 mg/dL in 30 minutes, or the like), an elevated glucose meal threshold (e.g., 200 mg/dL, 220 mg/dL, or the like), or the like. In some embodiments, machine learning classifiers (e.g., a decision tree) trained on prior meal-glucose responses may be utilized for triggering an Auto-Bolus. The meal detection threshold at the end of the period of fasting may be kept low (e.g., at a low end of a range, such as a rate of change of 15% or 195 mg/dL) for a short window (e.g., 40 minutes) starting from 20 minutes after dusk and ending at 60 minutes after dusk. Similarly, the meal detection threshold at the beginning of the period of fasting may be kept low for a longer window starting at dawn and ending at 60 minutes after dawn.

In an operational example, the controller of the drug delivery system such as that shown in FIG. 1 may have a processor that, when executing programming instructions to implement the processes and function described herein, may be operable to deliver a bolus dosage proximate to a beginning of the period of fasting and proximate to an end of the period of fasting.

For a further operational example, the processor, when delivering the bolus dosage prior to the beginning of the period of fasting, may initiate delivery of the bolus dosage in response to receipt of an indication, via the user interface (e.g., the user initiated bolus 611), that the period of fasting is beginning. Alternatively, when the processor is delivering the bolus dosage in response to the beginning of the period of fasting, the processor is further operable to initiate delivery of the bolus dosage upon receipt of a meal detection indication (e.g., Autobolus 631).

In yet a further operational example, when the processor is delivering the bolus dosage at the end of the period of fasting, the processor may be operable automatically initiate (e.g., the user interface initiated bolus 623) delivery of the bolus dosage at a predetermined time period proximate to the beginning of the period of fasting.

The other delivery modalities 613, 621, and 633 may be implemented in similar manners as those described above but with respect to their respective beginning time or end time for the period of fasting.

As discussed above with reference to FIG. 6, bolus insulin for the dawn meal can again be delivered similar to the dusk bolus, either by user initiation, or by time bound initiation (e.g., 30 minutes prior to dawn) or by AutoBolus based on meal detection.

Figure 7:
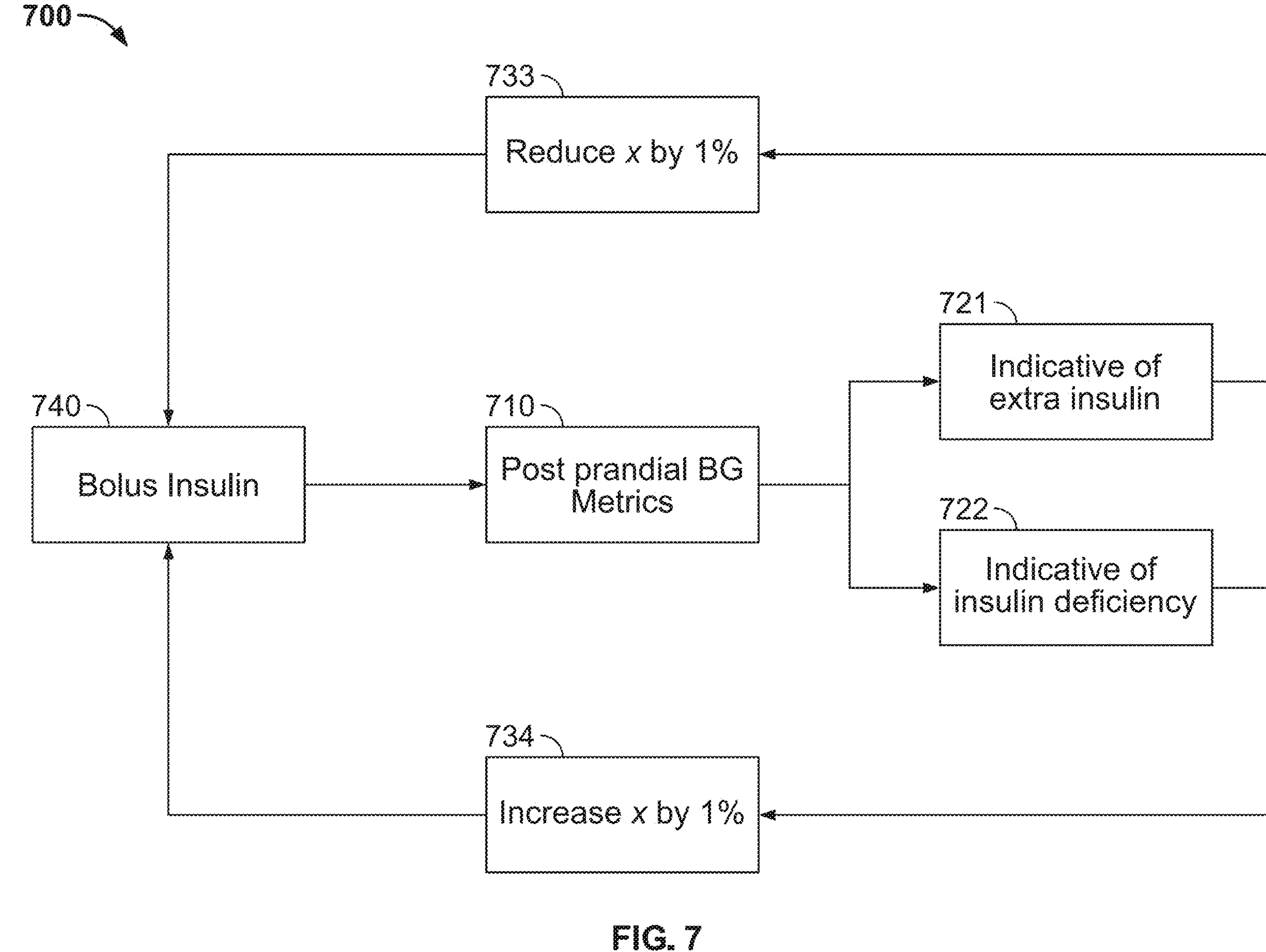
FIG. 7 illustrates a flowchart of an example process for adjusting bolus insulin based on the excursions in the glucose measurements.

FIG. 7 illustrates a flowchart of an example process for adjusting bolus insulin based on the excursions in the glucose level.

In the example of FIG. 7, the insulin delivered will follow the similar form described above with the value of x (of Equation 1 above) again being chosen as 10 (for a 10% TDI value in Equation 1). The bolus delivery 600 for dusk and dawn are illustrated in the example of FIG. 6.

The process 700 to evaluate the determination of a dosage for bolus insulin delivery may begin at 710. At 710, the processor may, for example, since a last bolus dosage, examine excursions in the glucose (BG) levels of the user as indicated by BG metrics determined from or based on data received from a continuous glucose sensor(s) or a glucose monitor. For example, at 710, the processor evaluate, for example, post prandial BG metrics that may include time above range (e.g., >180 mg/dl), time below range (e.g., <70 mg/dl), time T within range (e.g., 70 mg/dL<T<180 mg/dL), or the like. Depending on whether the evaluation of the post prandial BG metrics indicate extra insulin (721) or an insulin deficiency (722), the process 700 causes the processor to take a respective action to adjust the bolus insulin dosage and/or delivery schedule shown in FIG. 6. For example, in response to the indication of extra insulin at 721, the process 700 causes the processor to reduce x in Equation 1 above by 1. So, if x is initially 10, the processor would reduce x to 9 (for a 9% TDI value in Equation 1). The process 700 proceeds to 740 where a bolus dosage is calculated using Equation 1 with the 9% TDI value. Conversely, in response to the indication of insulin deficiency at 722, the process 700 causes the processor to increase x in Equation 1 above by 1. So, if x is initially 10, the processor would increase x to 11 (for a 11% TDI value in Equation 1). The process 700 proceeds to 740 where a bolus dosage is calculated using Equation 1 with the 11% TDI value. Process 700 may repeat approximately twice a day, three times a day or more, but may be less, to confirm that a proper bolus dosage is provided to compensate for meals outside the period of fasting.

Figure 8:
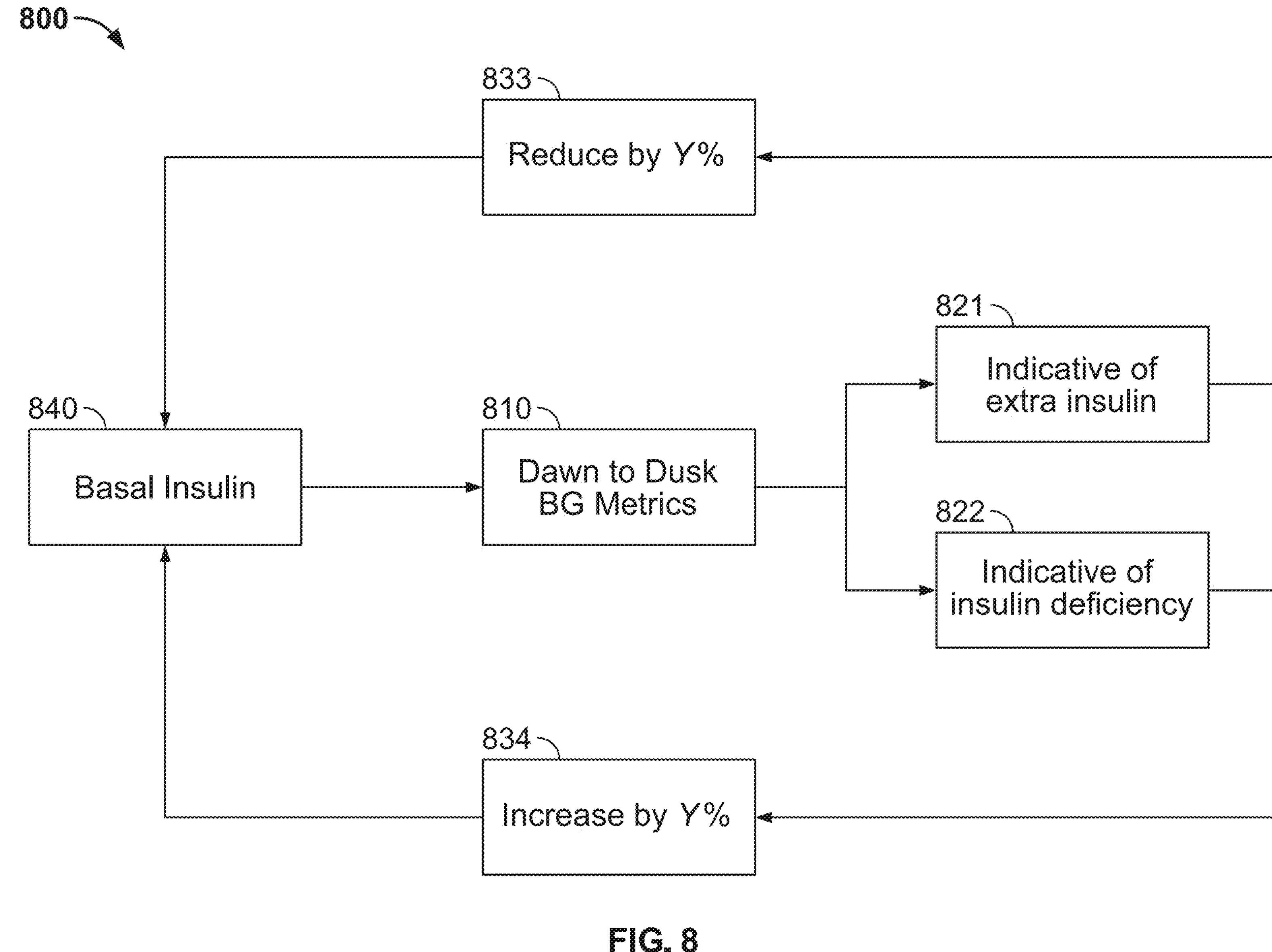
FIG. 8 illustrates a flowchart of an example process for adjusting basal insulin based on the excursions in the glucose measurements.

FIG. 8 illustrates a flowchart of an example process for adjusting basal insulin based on excursions in the glucose (BG) as indicated by BG metrics. For example, the process 800 may enable basal insulin dosages to be adjusted by examining (810) dawn to dusk BG metrics of the user determined from or based on data received from a continuous glucose sensor(s) or a glucose monitor. In the 810, the processor may evaluate, for example, the dawn-to-dusk BG metrics that may include time above range (>180 mg/dL), time below range (<70 mg/dL), time T within range (70 mg/dL<T<180 mg/dL), or the like. Depending on whether the evaluation of the dawn-to-dusk BG metrics indicate extra insulin (821) or an insulin deficiency (822), the process 800 takes a respective action to adjust the basal insulin dosage and/or delivery schedule. For example, in response to the indication of extra insulin at 821, the process 800 causes the processor to reduce basal insulin delivery by Y %, which may be a tunable variable and have values such as 2.5%, 2%, 3% or a range of values, such as 1%-2.5% or 1.5%-3%, or the like. In an example, if the basal insulin delivery during the fasting period was delivered according to the basal delivery schedule shown in FIG. 4A or 4B, the basal insulin delivered during the respective time marks by be reduced by Y %. Thus, the basal baseline may be reduced by Y % and the other percentages under/over the basal baseline may also be reduced. For example, if Y is 2.5, the 110% of 410 of FIG. 4A may be reduced to 107.5%. Conversely, in response to the indication of insulin deficiency at 822, the process 800 causes the processor to increase basal insulin delivery by Y %. For example, if Y is 2.5, the 110% of 410 of FIG. 4A may be increased to 112.5%.

The process 800 may repeat for each operational cycle of a drug delivery device during the period of fasting to confirm that a proper basal dosage is provided during the period of fasting, which in this example was dawn-to-dusk. Of course, other periods of fasting may be used, such as 6 hours (e.g., noon to 6 pm), 16 hours (8 pm until noon), 24 hours, 3 hours, 1 meal, 2 meals, 3 meals, or the like. A "meal" period of fasting (e.g., 1 meal) may be based on the assumption that the user typically eats three meals a day. So, a fasting period of "1 meal" may correspond to a continuous fasting period of 4 hours, 5 hours, or 6 hours, for example.

It is also envisioned that auxiliary sensors may be utilized to assist the fasting user with remaining within range during their period of fasting and for the number of days over which the user will be fasting. For example, Ramadan lasts 28-30 days during which the user is fasting.

Auxiliary sensor(s) that may be helpful during a fast is a ketone sensor, such as 196 or 196A of FIG. 1. A user when consuming a normal diet without fasting may have ketone levels that are typically approximately <0.5 mmol/L. Exercise and low carbohydrate levels can increase a user's ketone levels to approximately 3.0 mmol/L. Starvation ketosis may elevate ketone levels up to 5 mmol/L.

In an example, an ADD system may be equipped with a continuous subcutaneous ketone sensor, such as 196 or 196A of FIG. 1. For example, a concentration of 3-hydroxybutyrate can be measured using the 3-hydroxybutyrate dehydrogenase (3HBDH) enzyme which can be integrated with the CGM sensor. Hydrogel membranes have been used to improve ketone concentration and reduce electrode fouling.

Ketone levels with a physiological status are summarized in Table 2 below:

TABLE 2

Ketone Levels with Physiological Status

| Physiological Status | Ketone Level |
|---|---|
| Acceptable | 0-1.4 mmol/L |
| Above normal | 1.5-3.0 mmol/L |
| High | ≻3 mmol/L |
| Danger | ≻10 mmol/L |

In other examples, the ketone sensor and the CGM sensor may be integrated within the insulin delivery system as one physical unit. In still other examples, urine ketone levels or serum ketone levels may be used.

Auxiliary sensors may be used to monitor exercise of the user. Exercise monitoring may be accomplished via sensors, such as a heart rate monitor and/or accelerometer. The data from one or both of these sensors may provide data to related to an activity level and type of exercise performed by the user to the MDA. In other embodiments, activity data from fitness devices, such as a Fitbit® or the like, may be used.

Using a continuous glucose monitor and/or one or more of the auxiliary sensors the processor may be operable to perform safety monitoring and provide alerts to the user.

Figure 9:
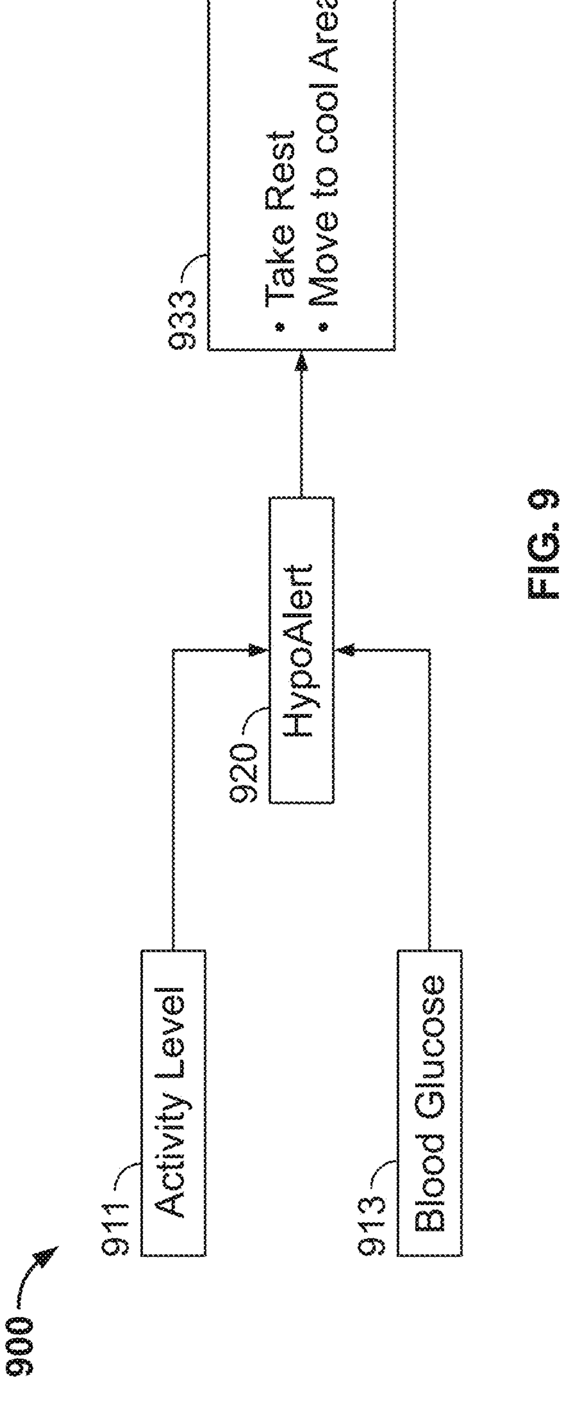
FIG. 9 is a process flow diagram illustrating the process flow that monitors for hypoglycemia and generates alerts based on the results of the monitoring.

FIG. 9 is a process flow diagram illustrating the process flow that monitors for hypoglycemia and generates alerts based on the results of the monitoring. The monitoring process 900 may be implemented when the processor enables a "HypoAlert" mode or similar type mode. For example, the processor may have different modes that utilize different algorithms to provide distinct functions related to the management of the user's glucose and diabetes. In the process 900 of FIG. 9, the processor may receive inputs from sensors that monitor a user's activity level 911, such as sensors 130, 133 and/or 134 of FIG. 1, and sensors that monitor the user's glucose levels, such as CGM 186 or 186A. An example of the indication of activity level may be low, medium, or high, or heart rate levels of 65 beats per minute (bpm), 95 bpm and 110 bpm may be respective thresholds for the low, medium, and high activity levels. For example, the activity level 911 and glucose levels 913 may be received by the processor and input to the hypoalert algorithm 920. The processor may be operable to execute the hypoalert algorithm 920. Based on the output of the hypoalert algorithm 920, the process 900 either performs step 933 or returns to 911 and 913.

For example, if the processor determines that the glucose is expected to fall below 70 mg/dl between the start of the period of fasting (e.g., dawn) until the end of the period of fasting (e.g., dusk), the processor may be operable to output via a graphical user interface an alert 933 to take rest and curtail physical activity (e.g., "move to a cool area" or the like). Also, if they are in unfavorable weather conditions (e.g., hot temperatures or the like), they will be encouraged to move to a favorable weather environment that allows the user to cool off. In addition, the processor may cause insulin delivery to be suspended or reduced to mitigate the hypoglycemic risk. Additional feedback provided via the GUI to the user may be to consider adding extra nutrition/balance in their pre-fast meals (e.g., pre-dawn meal) and post-fast meal (e.g., meal at dusk) to have better glycemic outcomes.

Other algorithms may provide different alerts such as a "RestAlert" and a "KetoAlert." In an example, a rest alert may be, similar to the hypoalert example of FIG. 9 and may be performed if the user is exerting themselves physically while starving for caloric intake or losing water, for example, due to excessive sweating, the rest alert process may cause the presentation of prompts to encourage the user to move to cooler environment and reduce physical activity, similar to the presentation of the prompts at 933 of FIG. 9.

Figure 10:
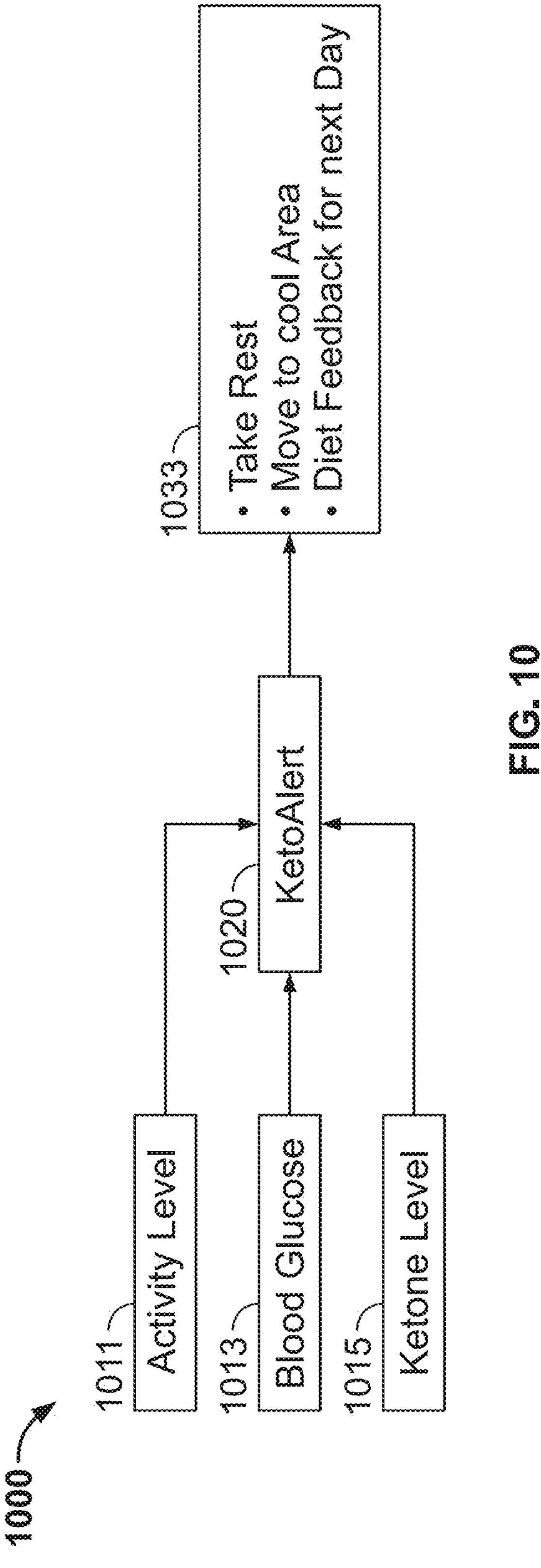
FIG. 10 is a process flow diagram illustrating the process flow that monitors for excessive ketone levels and generates alerts based on the results of the monitoring.

FIG. 10 illustrates a process flow diagram illustrating the process flow that monitors the user's ketone levels and generates an alert when the user's ketone levels are over a predetermined threshold. In addition to the HypoAlert and RestAlert processes, the processor may be operable to implement a "KetoAlert" process 1000 as shown in the example of FIG. 10. For example, the processor may receive inputs related to activity level 1013, glucose values 1015, and ketone levels 1017. The processor may use the inputs 1013, 1015 and 1017 in a ketoalert algorithm 1020. The ketoalert process 1020 may evaluate the activity level 1011 and glucose 1013 in a manner similar to the activity level 911 and glucose 913. With regard to the ketone level 1015, the processor may evaluate the ketone level 1015 provided by a ketone sensor(s), such as 196 or 196A of FIG. 1 and generate a ketoalert if the user's ketone levels are higher than 3 mmol/L or the like. In response to the ketoalert indicating the user's ketone levels are higher than 3 mmol/L, the processor at 1033 may cause a prompt on a GUI recommending the user to take a rest, move to a cooler area, and/or provide dietary feedback for the future or a following day. As feedback to the user also provided via the GUI, the processor may cause a recommendation to be presented on the GUI for the user to modify their dusk and dawn meals to be less prone to ketosis. In a further example, the processor may continue to monitor ketone levels closely and if the ketone levels rise above 10 mmol/L, the processor may be operable to request medical attention via communication circuitry coupled to the processor or may cause the generation of prompt as part of step 1033 for the user to seek medical attention. Should the ketoalert 1020 process not identify any activity, glucose or ketones above their respective alert thresholds, the process 1000 repeats with updated activity level data, glucose level data, and/or ketone level data.

Software related implementations of the techniques described herein, such as the processes examples described with reference to the above discussion and figures may include, but are not limited to, firmware, application specific software, or any other type of computer readable instructions that may be executed by one or more processors. The computer readable instructions may be provided via non-transitory computer-readable media. The various elements of the processes described with reference to the figures may be implemented in devices, apparatuses or systems that may include various hardware elements, software elements, or a combination of both. Examples of hardware elements may include structural members, logic devices, components, processors, microprocessors, circuits, processors, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), memory units, logic gates, registers, semiconductor device, chips, microchips, chip sets, and so forth. Examples of software elements may include software components, programs, applications, computer programs, application programs, system programs, software development programs, machine programs, operating system software, middleware, firmware, software modules, routines, subroutines, functions, processes, procedures, software interfaces, application program interfaces (API), instruction sets, computing code, computer code, code segments, computer code segments, words, values, symbols, or any combination thereof.

Some examples of the disclosed device or processes may be implemented, for example, using a storage medium, a computer-readable medium, or an article of manufacture which may store an instruction or a set of instructions that, if executed by a machine (i.e., processor or controller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosure were described above. It is, however, expressly noted that the present disclosure is not limited to those examples, but rather the intention is that additions and modifications to what was expressly described herein are also included within the scope of the disclosed examples. Moreover, it is to be understood that the features of the numerous examples described herein were not mutually exclusive and may exist in various combinations and permutations, even if such combinations or permutations were not made express herein, without departing from the spirit and scope of the disclosed examples. In fact, variations, modifications, and other implementations of what was described herein will occur to those of ordinary skill in the art without departing from the spirit and the scope of the disclosed examples. As such, the disclosed examples are not to be defined only by the preceding illustrative description.

Program aspects of the technology may be thought of as "products" or "articles of manufacture" typically in the form of executable code and/or associated data that is carried on or embodied in a type of non-transitory, machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, novel subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of examples has been presented for the purposes of illustration and description. It is not intended to be exhaustive or to limit the present disclosure to the precise forms disclosed. Many modifications and variations are possible considering this disclosure. It is intended that the scope of the present disclosure be limited not by this detailed description, but by the claims appended hereto. Future filed applications claiming priority to this application may claim the disclosed subject matter in a different manner and may include any set of one or more features as variously disclosed or otherwise demonstrated herein.

What is claimed is:

1. A controller of a drug delivery system, comprising:

a processor operable to execute programming instructions;

a user interface including a display and user input circuitry;

a memory operable to store the programming instructions; and a communication circuitry coupled to the processor operable to receive and transmit wireless communication signals, wherein the processor is operable to:

receive, via the user interface, an indication of fasting event or a period of fasting for a user; and modify a drug delivery schedule based on the period of fasting to increase a basal delivery rate for a first time threshold after receipt of the indication.

2. The controller of the drug delivery system of claim 1, wherein the processor, when modifying the drug delivery schedule based on the period of fasting, is further operable to:

maintain a basal delivery rate at a baseline value between a first time threshold after receipt of the indication of the period of fasting and a second time threshold after receipt of the indication of the period of fasting.

3. The controller of the drug delivery system of claim 1, wherein the processor, when modifying the drug delivery schedule based on the period of fasting, is further operable to:

reduce a basal delivery rate for a period of time prior to an end of the period of fasting.

4. The controller of the drug delivery system of claim 1, wherein the processor is further operable to:

deliver a bolus dosage in close proximity to an end of the period of fasting.

5. The controller of the drug delivery system of claim 4, wherein the processor, when delivering the bolus dosage in response to the end of the period of fasting, is further operable to:

initiate delivery of the bolus dosage in response to receipt of an indication, via the user interface, that the period of fasting has ended.

6. The controller of the drug delivery system of claim 4, wherein the processor, when delivering the bolus dosage at the end of the period of fasting, is further operable to:

initiate delivery of the bolus dosage automatically in response to the end of the period of fasting.

7. The controller of the drug delivery system of claim 4, wherein the processor, when delivering the bolus dosage in response to the end of the period of fasting, is further operable to:

automatically initiate delivery of the bolus dosage upon receipt of a meal detection indication.

8. The controller of the drug delivery system of claim 1, wherein the processor is further operable to:

deliver a bolus dosage proximate to a beginning of the period of fasting.

9. The controller of the drug delivery system of claim 8, wherein the processor, when delivering the bolus dosage prior to the beginning of the period of fasting, is further operable to:

initiate delivery of the bolus dosage in response to receipt of an indication, via the user interface, that the period of fasting is beginning.

10. The controller of the drug delivery system of claim 8, wherein the processor, when delivering the bolus dosage at the end of the period of fasting, is further operable to:

automatically initiate delivery of the bolus dosage at a predetermined time period proximate to the beginning of the period of fasting.

11. The controller of the drug delivery system of claim 8, wherein the processor, when delivering the bolus dosage in response to the beginning of the period of fasting, is further operable to:

initiate delivery of the bolus dosage upon receipt of a meal detection indication.

12. The controller of the drug delivery system of claim 1, wherein the processor, when modifying the drug delivery schedule based on the period of fasting, is further operable to:

adjust a basal delivery rate according to a function that decreases the basal rate delivery from a set percentage increase of a baseline basal delivery rate down to the baseline basal delivery rate, and from the baseline basal delivery rate to the set percentage or another set percentage under the baseline basal delivery rate during the period of fasting.

13. The controller of the drug delivery system of claim 1, wherein the processor, when modifying the drug delivery schedule based on the period of fasting, is further operable to:

at an end of the period of fasting, adjust a basal delivery rate to a basal rate delivery increased by a set percentage over a baseline basal rate for a first period of time, set the basal delivery rate to the baseline basal rate delivery for a second period of time, and increase the baseline basal delivery rate by the preset percentage over the baseline basal delivery rate for a third period of time.

14. The controller of the drug delivery system of claim 1, wherein the processor, when modifying the drug delivery schedule based on the period of fasting, is further operable to:

at an end of the period of fasting, adjust a basal delivery rate according to a function that decreases a basal delivery rate from a preset percentage increase over a baseline basal delivery rate to the baseline basal delivery rate over a first period of time, maintain the basal delivery rate at the baseline basal delivery rate for a second period of time, and increase the basal delivery rate again by the preset percentage over baseline basal delivery rate for a third period of time.

15. A drug delivery system, comprising:

a processor operable to execute programming instructions;

a user interface including a display and user input circuitry;

a memory operable to store the programming instructions; and a communication circuitry coupled to the processor operable to receive and transmit wireless communication signals, wherein the processor is operable to:

receive, via the user interface, an indication of a period of fasting for a user; and modify a drug delivery schedule based on the period of fasting to increase a basal delivery rate for a first time threshold after receipt of the indication.

16. The drug delivery system of claim 15, wherein the processor, when modifying the drug delivery schedule based on the period of fasting, is further operable to:

maintain a basal delivery rate at a baseline value between a first time threshold after receipt of the indication of the period of fasting and a second time threshold after receipt of the indication of the period of fasting.

17. The drug delivery system of claim 15, wherein the processor, when modifying the drug delivery schedule based on the period of fasting, is further operable to:

reduce a basal delivery rate for a period of time prior to an end of the period of fasting.

18. The drug delivery system of claim 15, wherein the processor is further operable to:

deliver a bolus dosage in close proximity to an end of the period of fasting.

* * * * *